(12) United States Patent
Dillard et al.

(10) Patent No.: US 7,875,048 B2
(45) Date of Patent: Jan. 25, 2011

(54) ONE-WAY VALVE DEVICES FOR ANCHORED IMPLANTATION IN A LUNG

(75) Inventors: David H. Dillard, Redmond, WA (US); Hugo X. Gonzalez, Woodinville, WA (US); Seung Yi, Bothell, WA (US); Lauri J. DeVore, Seattle, WA (US); Mia Park, Redmond, WA (US); Dean T. Corcoran, Bothell, WA (US); Jenni Rimbaugh, Bothell, WA (US); Clifton A. Alferness, Redmond, WA (US)

(73) Assignee: Spiration, Inc., Redmond, WA (US)

( * ) Notice: Subject to any disclaimer, the term of this patent is extended or adjusted under 35 U.S.C. 154(b) by 906 days.

(21) Appl. No.: 10/933,778

(22) Filed: Sep. 3, 2004

(65) Prior Publication Data

US 2005/0033344 A1 Feb. 10, 2005

Related U.S. Application Data

(63) Continuation of application No. 10/150,547, filed on May 17, 2002, now abandoned.

(51) Int. Cl.
*A61M 29/00* (2006.01)
(52) U.S. Cl. .................................... 606/191; 623/23.64
(58) Field of Classification Search ................. 606/95, 606/108, 190, 191, 198; 623/23.64, 23.65; 128/207.15, 200.24
See application file for complete search history.

(56) References Cited

U.S. PATENT DOCUMENTS

| | | | |
|---|---|---|---|
| 2,981,254 A | 4/1961 | Vanderbilt | |
| 3,540,431 A | 11/1970 | Mobin-Uddin | |
| 3,617,060 A | 11/1971 | Lezzi | |

(Continued)

FOREIGN PATENT DOCUMENTS

DE 100 04 979 8/2000

(Continued)

OTHER PUBLICATIONS

U.S. Appl. No. 10/387,963, filed Mar. 12, 2003, Gordon et al.

(Continued)

*Primary Examiner*—Gary Jackson
*Assistant Examiner*—Victor X Nguyen
(74) *Attorney, Agent, or Firm*—Knobbe, Martens, Olson & Bear LLP

(57) ABSTRACT

An intra-bronchial device placed and anchored in an air passageway of a patient to collapse a lung portion associated with the air passageway. The device includes a support structure, an obstructing member carried by the support structure that reduces ventilation to the lung portion by preventing air from being inhaled into the lung portion, and at least one anchor carried by the support structure that anchors the obstruction device within the air passageway. The anchor may engage the air passageway wall by piercing or friction, include a stop dimensioned for limiting the piercing of the air passageway wall, and may be releasable from the air passageway for removal of the intra-bronchial device. The anchors may be carried by a peripheral portion of the support structure, or by a central portion of the support structure. The obstructing member may be a one-way valve.

35 Claims, 10 Drawing Sheets

U.S. PATENT DOCUMENTS

| | | | |
|---|---|---|---|
| 3,657,744 A | 4/1972 | Ersek | |
| 3,760,808 A | 9/1973 | Bleuer | |
| 3,788,327 A | 1/1974 | Donowitz et al. | |
| 3,874,388 A | 4/1975 | King et al. | |
| 4,014,318 A | 3/1977 | Dockum et al. | |
| 4,056,854 A | 11/1977 | Boretos et al. | |
| 4,086,665 A | 5/1978 | Poirier | |
| 4,212,463 A | 7/1980 | Repinski et al. | |
| 4,250,873 A | 2/1981 | Bonnet | |
| 4,301,810 A | 11/1981 | Belman | |
| 4,302,854 A | 12/1981 | Runge | |
| 4,610,256 A | 9/1986 | Wallace | |
| 4,619,246 A | 10/1986 | Molgaard-Nielsen et al. | |
| 4,654,027 A | 3/1987 | Dragan et al. | |
| 4,681,110 A | 7/1987 | Wiktor | |
| 4,684,363 A | 8/1987 | Ari et al. | |
| 4,710,192 A | 12/1987 | Liotta et al. | |
| 4,727,873 A | 3/1988 | Mobin-Uddin | |
| 4,732,152 A | 3/1988 | Wallsten et al. | |
| 4,745,925 A | 5/1988 | Dietz | |
| 4,759,758 A | 7/1988 | Gabbay | |
| 4,795,449 A | 1/1989 | Schneider et al. | |
| 4,808,183 A | 2/1989 | Panje | |
| 4,819,664 A | 4/1989 | Nazari | |
| 4,830,003 A | 5/1989 | Wolff et al. | |
| 4,832,680 A | 5/1989 | Haber et al. | |
| 4,846,836 A | 7/1989 | Reich | |
| 4,850,999 A | 7/1989 | Planck | |
| 4,852,568 A | 8/1989 | Kensey | |
| 4,877,025 A | 10/1989 | Hanson | |
| 4,908,028 A | 3/1990 | Colon et al. | |
| 4,934,999 A | 6/1990 | Bader | |
| 4,968,294 A | 11/1990 | Salama | |
| 5,059,208 A | 10/1991 | Coe et al. | |
| 5,061,274 A | 10/1991 | Kensey | |
| 5,116,360 A | 5/1992 | Pinchuk et al. | |
| 5,116,564 A | 5/1992 | Jansen et al. | |
| 5,123,919 A | 6/1992 | Sauter et al. | |
| 5,151,105 A | 9/1992 | Kwan-Gett | |
| 5,158,548 A | 10/1992 | Lau et al. | |
| 5,161,524 A | 11/1992 | Evans | |
| 5,171,299 A | 12/1992 | Heitzmann et al. | |
| 5,255,687 A | 10/1993 | McKenna | |
| 5,283,063 A | 2/1994 | Freeman | |
| 5,304,199 A | 4/1994 | Myers | |
| 5,306,234 A | 4/1994 | Johnson | |
| 5,314,473 A | 5/1994 | Godin | |
| 5,339,805 A | 8/1994 | Parker | |
| 5,342,298 A | 8/1994 | Michaels | |
| 5,352,240 A | 10/1994 | Ross | |
| 5,358,518 A | 10/1994 | Camilli | |
| 5,366,478 A | 11/1994 | Brinkerhoff et al. | |
| 5,370,657 A * | 12/1994 | Irie | 606/200 |
| 5,382,261 A | 1/1995 | Palmaz | |
| 5,392,775 A | 2/1995 | Adkins, Jr. et al. | |
| 5,398,844 A | 3/1995 | Zaslavsky | |
| 5,409,019 A | 4/1995 | Wilk | |
| 5,411,507 A | 5/1995 | Heckele | |
| 5,411,552 A | 5/1995 | Andersen et al. | |
| 5,413,599 A | 5/1995 | Imachi et al. | |
| 5,417,226 A | 5/1995 | Juma | |
| 5,445,626 A | 8/1995 | Gigante | |
| 5,453,090 A | 9/1995 | Martinez et al. | |
| 5,486,154 A | 1/1996 | Kelleher | |
| 5,499,995 A | 3/1996 | Teirstein | |
| 5,500,014 A | 3/1996 | Quijano et al. | |
| 5,507,754 A | 4/1996 | Green et al. | |
| 5,509,900 A | 4/1996 | Kirkman | |
| 5,549,626 A | 8/1996 | Miller et al. | |
| 5,549,628 A | 8/1996 | Cooper et al. | |
| 5,562,608 A | 10/1996 | Sekins et al. | |
| 5,562,728 A | 10/1996 | Lazarus et al. | |
| 5,603,698 A | 2/1997 | Roberts et al. | |
| 5,645,565 A | 7/1997 | Rudd et al. | |
| 5,660,175 A | 8/1997 | Dayal | |
| 5,662,713 A | 9/1997 | Andersen et al. | |
| 5,669,933 A * | 9/1997 | Simon et al. | 600/200 |
| 5,683,451 A | 11/1997 | Lenker et al. | |
| 5,693,089 A | 12/1997 | Inoue | |
| 5,697,968 A | 12/1997 | Rogers et al. | |
| 5,702,409 A | 12/1997 | Rayburn et al. | |
| 5,725,519 A | 3/1998 | Penner et al. | |
| 5,752,522 A | 5/1998 | Murphy | |
| 5,752,965 A | 5/1998 | Francis et al. | |
| 5,755,770 A | 5/1998 | Ravenscroft | |
| 5,797,960 A | 8/1998 | Stevens et al. | |
| 5,800,339 A | 9/1998 | Salama | |
| 5,803,078 A | 9/1998 | Brauner | |
| 5,817,101 A | 10/1998 | Fiedler | |
| 5,833,694 A | 11/1998 | Poncet | |
| 5,840,081 A | 11/1998 | Andersen et al. | |
| 5,851,232 A | 12/1998 | Lois | |
| 5,855,587 A | 1/1999 | Hyon et al. | |
| 5,855,597 A | 1/1999 | Jayaraman | |
| 5,855,601 A | 1/1999 | Bessler et al. | |
| 5,876,445 A | 3/1999 | Andersen et al. | |
| 5,925,063 A | 7/1999 | Khosravi | |
| 5,944,738 A | 8/1999 | Amplatz et al. | |
| 5,947,997 A | 9/1999 | Pavcnik et al. | |
| 5,954,636 A | 9/1999 | Schwartz et al. | |
| 5,954,766 A | 9/1999 | Zadno-Azizi et al. | |
| 5,957,949 A | 9/1999 | Leonhardt et al. | |
| 5,972,009 A | 10/1999 | Fortier et al. | |
| 5,976,158 A | 11/1999 | Adams et al. | |
| 5,976,174 A | 11/1999 | Ruiz | |
| 5,984,965 A | 11/1999 | Knapp et al. | |
| 6,003,517 A | 12/1999 | Sheffield et al. | |
| 6,007,575 A | 12/1999 | Samuels | |
| 6,009,614 A | 1/2000 | Morales | |
| 6,010,525 A | 1/2000 | Bonutti et al. | |
| 6,020,380 A | 2/2000 | Killian | |
| 6,027,525 A | 2/2000 | Suh et al. | |
| 6,045,560 A | 4/2000 | McKean et al. | |
| 6,051,022 A | 4/2000 | Cai et al. | |
| 6,068,635 A | 5/2000 | Gianotti | |
| 6,068,638 A | 5/2000 | Makower | |
| 6,077,291 A | 6/2000 | Das | |
| 6,083,141 A | 7/2000 | Hougen | |
| 6,083,255 A | 7/2000 | Laufer et al. | |
| 6,096,027 A | 8/2000 | Layne | |
| 6,099,551 A | 8/2000 | Gabbay | |
| 6,123,663 A | 9/2000 | Rebuffat | |
| 6,132,458 A | 10/2000 | Staehle et al. | |
| 6,135,729 A | 10/2000 | Aber | |
| 6,135,991 A | 10/2000 | Muni et al. | |
| 6,141,855 A | 11/2000 | Morales | |
| 6,149,664 A | 11/2000 | Kurz | |
| 6,162,245 A | 12/2000 | Jayaraman | |
| 6,165,179 A | 12/2000 | Cathcart et al. | |
| 6,168,614 B1 | 1/2001 | Andersen et al. | |
| 6,168,617 B1 | 1/2001 | Blaeser et al. | |
| 6,174,307 B1 | 1/2001 | Daniel et al. | |
| 6,174,323 B1 | 1/2001 | Biggs et al. | |
| 6,183,520 B1 | 2/2001 | Pintauro et al. | |
| 6,193,748 B1 | 2/2001 | Thompson et al. | |
| 6,200,333 B1 | 3/2001 | Laufer | |
| 6,203,551 B1 | 3/2001 | Wu | |
| 6,206,918 B1 | 3/2001 | Campbell et al. | |
| 6,231,589 B1 * | 5/2001 | Wessman et al. | 606/200 |
| 6,234,996 B1 | 5/2001 | Bagaoisan et al. | |
| 6,238,334 B1 | 5/2001 | Easterbrook, III et al. | |
| 6,240,615 B1 | 6/2001 | Kimes et al. | |
| 6,242,472 B1 | 6/2001 | Sekins et al. | |
| 6,245,102 B1 | 6/2001 | Jayaraman | |

| | | |
|---|---|---|
| 6,258,100 B1 | 7/2001 | Alferness et al. |
| 6,264,700 B1 | 7/2001 | Kilcoyne et al. |
| 6,267,775 B1 | 7/2001 | Clerc et al. |
| 6,270,527 B1 | 8/2001 | Campbell et al. |
| 6,287,290 B1 | 9/2001 | Perkins et al. |
| 6,287,334 B1 | 9/2001 | Moll et al. |
| 6,293,951 B1 | 9/2001 | Alferness et al. |
| 6,302,893 B1 | 10/2001 | Limon et al. |
| 6,312,407 B1 | 11/2001 | Zadno-Azizi et al. |
| 6,325,777 B1 | 12/2001 | Zadno-Azizi et al. |
| 6,325,778 B1 | 12/2001 | Zadno-Azizi et al. |
| 6,327,772 B1 | 12/2001 | Zadno-Azizi et al. |
| 6,328,689 B1 | 12/2001 | Gonzalez et al. |
| 6,350,278 B1 | 2/2002 | Lenker et al. |
| 6,355,014 B1 | 3/2002 | Zadno-Azizi et al. |
| 6,398,775 B1 | 6/2002 | Perkins et al. |
| 6,402,754 B1 | 6/2002 | Gonzalez |
| 6,416,554 B1 | 7/2002 | Alferness et al. |
| 6,425,916 B1 | 7/2002 | Garrison et al. |
| 6,428,561 B1 | 8/2002 | Johansson-Ruden et al. |
| 6,439,233 B1 | 8/2002 | Geertsema |
| 6,447,530 B1 | 9/2002 | Ostrovsky et al. |
| 6,454,754 B1 | 9/2002 | Frank |
| 6,458,076 B1 | 10/2002 | Pruitt |
| 6,471,718 B1 | 10/2002 | Staehle et al. |
| 6,471,979 B2 | 10/2002 | New et al. |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,493,589 B1 | 12/2002 | Medhkour et al. |
| 6,503,272 B2 | 1/2003 | Duerig et al. |
| 6,510,846 B1 | 1/2003 | O'Rourke |
| 6,514,290 B1 | 2/2003 | Loomas |
| 6,527,761 B1 | 3/2003 | Soltesz et al. |
| 6,540,782 B1 | 4/2003 | Snyders |
| 6,544,192 B2 | 4/2003 | Starr et al. |
| 6,558,429 B2 | 5/2003 | Taylor |
| 6,568,387 B2 | 5/2003 | Davenport et al. |
| 6,569,166 B2 | 5/2003 | Gonzalez |
| 6,585,639 B1 | 7/2003 | Kotmel et al. |
| 6,589,256 B2 | 7/2003 | Forber |
| 6,592,594 B2 | 7/2003 | Rimbaugh et al. |
| 6,599,311 B1 | 7/2003 | Biggs et al. |
| 6,610,043 B1 | 8/2003 | Ingenito |
| 6,629,951 B2 | 10/2003 | Laufer et al. |
| 6,634,363 B1 | 10/2003 | Danek et al. |
| 6,638,285 B2 | 10/2003 | Gabbay |
| 6,679,264 B1 | 1/2004 | Deem et al. |
| 6,682,250 B2 | 1/2004 | Banks |
| 6,682,520 B2 | 1/2004 | Ingenito |
| 6,694,979 B2 * | 2/2004 | Deem et al. ............ 128/207.14 |
| 6,709,401 B2 | 3/2004 | Perkins et al. |
| 6,712,812 B2 | 3/2004 | Roschak et al. |
| 6,716,208 B2 | 4/2004 | Humes |
| 6,722,360 B2 | 4/2004 | Doshi |
| 6,743,259 B2 | 6/2004 | Ginn |
| 6,746,686 B2 | 6/2004 | Hughes et al. |
| 6,749,606 B2 | 6/2004 | Keast et al. |
| 6,840,952 B2 | 1/2005 | Saker et al. |
| 6,860,847 B2 | 3/2005 | Alferness et al. |
| 6,904,909 B2 | 6/2005 | Andreas et al. |
| 6,929,637 B2 * | 8/2005 | Gonzalez et al. ......... 604/890.1 |
| 6,941,950 B2 | 9/2005 | Wilson et al. |
| 7,011,094 B2 * | 3/2006 | Rapacki et al. ........ 128/207.15 |
| 7,412,977 B2 | 8/2008 | Fields et al. |
| 7,434,578 B2 | 10/2008 | Dillard et al. |
| 2001/0010017 A1 | 7/2001 | Letac et al. |
| 2001/0025132 A1 | 9/2001 | Alferness et al. |
| 2001/0034518 A1 | 10/2001 | Edwards et al. |
| 2001/0037808 A1 | 11/2001 | Deem et al. |
| 2001/0041906 A1 | 11/2001 | Gonzalez |
| 2001/0052344 A1 | 12/2001 | Doshi |
| 2001/0056274 A1 | 12/2001 | Perkins et al. |
| 2002/0007831 A1 | 1/2002 | Davenport et al. |
| 2002/0052626 A1 | 5/2002 | Gilson |
| 2002/0062120 A1 | 5/2002 | Perkins et al. |
| 2002/0077593 A1 | 6/2002 | Perkins et al. |
| 2002/0077696 A1 | 6/2002 | Zadno-Azizi et al. |
| 2002/0087153 A1 | 7/2002 | Roschak et al. |
| 2002/0095209 A1 | 7/2002 | Zadno-Azizi et al. |
| 2002/0111619 A1 | 8/2002 | Keast et al. |
| 2002/0111620 A1 | 8/2002 | Cooper et al. |
| 2002/0112729 A1 | 8/2002 | DeVore et al. |
| 2002/0138135 A1 | 9/2002 | Duerig et al. |
| 2002/0147462 A1 | 10/2002 | Mair et al. |
| 2003/0013935 A1 | 1/2003 | Alferness et al. |
| 2003/0018327 A1 | 1/2003 | Truckai et al. |
| 2003/0018344 A1 | 1/2003 | Kaji et al. |
| 2003/0050648 A1 | 3/2003 | Alferness et al. |
| 2003/0051733 A1 | 3/2003 | Kotmel et al. |
| 2003/0055331 A1 | 3/2003 | Kotmel et al. |
| 2003/0070682 A1 | 4/2003 | Wilson et al. |
| 2003/0125763 A1 | 7/2003 | McInnes |
| 2003/0127090 A1 | 7/2003 | Gifford et al. |
| 2003/0154988 A1 | 8/2003 | DeVore |
| 2003/0158515 A1 | 8/2003 | Gonzalez |
| 2003/0167065 A1 | 9/2003 | Kumar |
| 2003/0180922 A1 | 9/2003 | Alferness |
| 2003/0183235 A1 | 10/2003 | Rimbaugh et al. |
| 2003/0195385 A1 | 10/2003 | DeVore |
| 2003/0212412 A1 | 11/2003 | Dillard et al. |
| 2003/0216769 A1 | 11/2003 | Dillard et al. |
| 2003/0228344 A1 | 12/2003 | Fields et al. |
| 2004/0039250 A1 | 2/2004 | Tholfsen et al. |
| 2004/0167636 A1 | 8/2004 | Dillard et al. |
| 2004/0243140 A1 | 12/2004 | Alferness et al. |
| 2005/0033310 A1 | 2/2005 | Alferness et al. |
| 2005/0137611 A1 | 6/2005 | Escudero et al. |
| 2005/0166925 A1 | 8/2005 | Wilson et al. |
| 2005/0222580 A1 | 10/2005 | Gifford, III et al. |
| 2005/0267323 A1 | 12/2005 | Dorros et al. |

FOREIGN PATENT DOCUMENTS

| | | |
|---|---|---|
| EP | 1151729 | 11/2001 |
| EP | 1157663 | 11/2001 |
| GB | 324 729 | 11/1998 |
| JP | 58-163332 | 9/1983 |
| JP | 60-10740 | 1/1994 |
| JP | 2003-503162 | 1/2003 |
| RU | 2140211 | 10/1999 |
| SU | 852321 | 7/1981 |
| WO | WO 88/09683 | 12/1988 |
| WO | WO 94/26175 | 11/1994 |
| WO | 95/32018 | 11/1995 |
| WO | WO 96/34582 | 11/1996 |
| WO | WO 97/44085 | 11/1997 |
| WO | WO 98/00840 | 1/1998 |
| WO | WO 98/19633 | 5/1998 |
| WO | PCT/US98/18366 | 9/1998 |
| WO | WO 98/39047 | 9/1998 |
| WO | WO 98/44854 | 10/1998 |
| WO | PCT/GB98/00652 | 11/1998 |
| WO | WO 98/48706 | 11/1998 |
| WO | WO 99/01076 | 1/1999 |
| WO | 99/13801 | 3/1999 |
| WO | WO 99/26692 | 6/1999 |
| WO | 99/32040 | 7/1999 |
| WO | WO 99/42059 | 8/1999 |
| WO | WO 99/42161 | 8/1999 |
| WO | WO 99/64109 | 12/1999 |
| WO | WO 00/42950 | 7/2000 |
| WO | WO 00/51510 | 9/2000 |
| WO | 00/62699 | 10/2000 |
| WO | WO 00/78386 | 12/2000 |
| WO | WO/00/78407 | 12/2000 |

| | | | | | |
|---|---|---|---|---|---|
| WO | WO 00/78407 | 12/2000 | WO | 2004/010845 | 5/2004 |

OTHER PUBLICATIONS

| | | |
|---|---|---|
| WO | 01/03642 | 1/2001 |
| WO | PCT/US00/18286 | 1/2001 |
| WO | WO 01/02042 | 1/2001 |
| WO | WO 01/05334 | 1/2001 |
| WO | WO 01/10313 | 2/2001 |
| WO | WO 01/10314 | 2/2001 |
| WO | WO 01/13839 | 3/2001 |
| WO | WO 01/13908 | 3/2001 |
| WO | 01/28433 | 4/2001 |
| WO | WO 01/12104 | 5/2001 |
| WO | WO 01/45590 | 6/2001 |
| WO | WO 01/49213 | 7/2001 |
| WO | WO 01/52775 | 7/2001 |
| WO | WO 01/54585 | 8/2001 |
| WO | WO 01/54625 | 8/2001 |
| WO | WO 01/54685 | 8/2001 |
| WO | PCT/US01/06958 | 9/2001 |
| WO | WO 01/66190 | 9/2001 |
| WO | 01/74271 | 10/2001 |
| WO | 01/89366 | 11/2001 |
| WO | PCT/NZ01/00092 | 11/2001 |
| WO | WO 01/87170 | 11/2001 |
| WO | WO 02/05884 | 1/2002 |
| WO | PCT/US01/28360 | 3/2002 |
| WO | WO 02/22072 | 3/2002 |
| WO | WO 02/32333 | 4/2002 |
| WO | 02/34322 | 5/2002 |
| WO | WO 02/38038 | 5/2002 |
| WO | WO 02/47575 | 6/2002 |
| WO | WO 02/056794 | 7/2002 |
| WO | 02/064045 | 8/2002 |
| WO | WO 02/064190 | 8/2002 |
| WO | WO 02/069823 | 9/2002 |
| WO | 02/094087 | 11/2002 |
| WO | 01/95786 | 12/2002 |
| WO | WO 03/022124 | 3/2003 |
| WO | WO 03/030975 | 4/2003 |
| WO | WO 03/34927 | 5/2003 |
| WO | WO 03/041779 | 5/2003 |
| WO | WO 03/047468 | 6/2003 |
| WO | WO 03/078579 | 9/2003 |
| WO | WO 03/088820 | 10/2003 |
| WO | WO 03/099164 | 12/2003 |
| WO | WO 2004/010845 | 2/2004 |

U.S. Appl. No. 10/847,554, filed May 17, 2004, Alferness et al.
U.S. Appl. No. 10/847,427, filed May 17, 2004, Alferness et al.
U.S. Appl. No. 10/746,981, filed Feb. 10, 2005, Dillard et al.
Article: Autocath 100—Nonsurgical, Intraurethral Bladder Control Device for Incontinent and Retentive Women—Dr. Kulisz's Development.
Dillard et al., Evaluation of a Novel Intra-bronchial Valve Device to Produce Lunch Volume Reduction,, Poster shown at conf in Jun. 2002.
EWS Endobronchial Watanabe Spigots, Novatech, edited Apr. 17, 2002.
Harris et al., The Experimental Production in Dogs of Emphysema with Associated Asthmatic Syndrome by Means of an Intertracheal Ball Valve, J. Exp Med 30:1919; 75-88.
Horiuchi et al., Three Cases of Intractable Pneumothorax Treated Successfully by Bronchial Embolization using Silicon, JJSB, 2001. pp. 25-30.
Inaspettato: Endoscopic Treatment of Bronchopleural Fistulas Using N-butyl-2-cyanoacrylate; Surgical Laparoscopy & Endoscopy; vol. 1, pp. 62-64, 1994.
Jones et al., Closure of a Benign Broncho-Oesophageal Fistula by Endoscopic Injection of Bovine Collagen, Cyanocrylate Glue and Gelfoam; 1996, pp. 53-55 Aust. N.Z. J. Surg.
Lewis et al., Pulmonary Interstitial Emphysema: Selective Bronchial Occlusion with a SwanGanz Catheter, Archives of Disease in Childhood, 63:1988, 313-315.
Matthew et al., Selective Bronchial Obstruction for Treatment of Bullous Interstitial Emphysema, J. of Ped. 96:1980, 475-477.
Okada et al., Emergent Bronchofiberoptic Bronchial Occlusion for Intractable Pneumothorax with Severe Emphysema; The Japanese Journal of Thoracic and Cardiovascular Surgery, 1998, pp. 1078-1081.
Puhakka et al., Acute Bronchial Obstruction: An Experimental Rabbit Model Study, Int. J. of Pediatric Otorhinolaryngology, 18:1989, 107-118.
Snider et al., The Definition of Emphysema: Report of the National Heart Lung and Blood Instiute, Division of Lung Diseases Workshop, Am. Rev. Respir. Dis., 132:182-185, 1985.
Watanabe et al., Bronchial Embolization Using Dental Impression Material in a Case of Pyelo-bronchial Fistula with Candida Fungemia; 1991, Journal of Japan Society for Bronchology, pp. 607-610.
U.S. Appl. No. 10/848,571, filed May 17, 2004, Alferness et al.
Ellis, James H., Balloon Catheter Occlusion of Bronchopleural Fistulae, May 7, 1981, AJR: 138, Jan. 1982, p. 157-159.

* cited by examiner

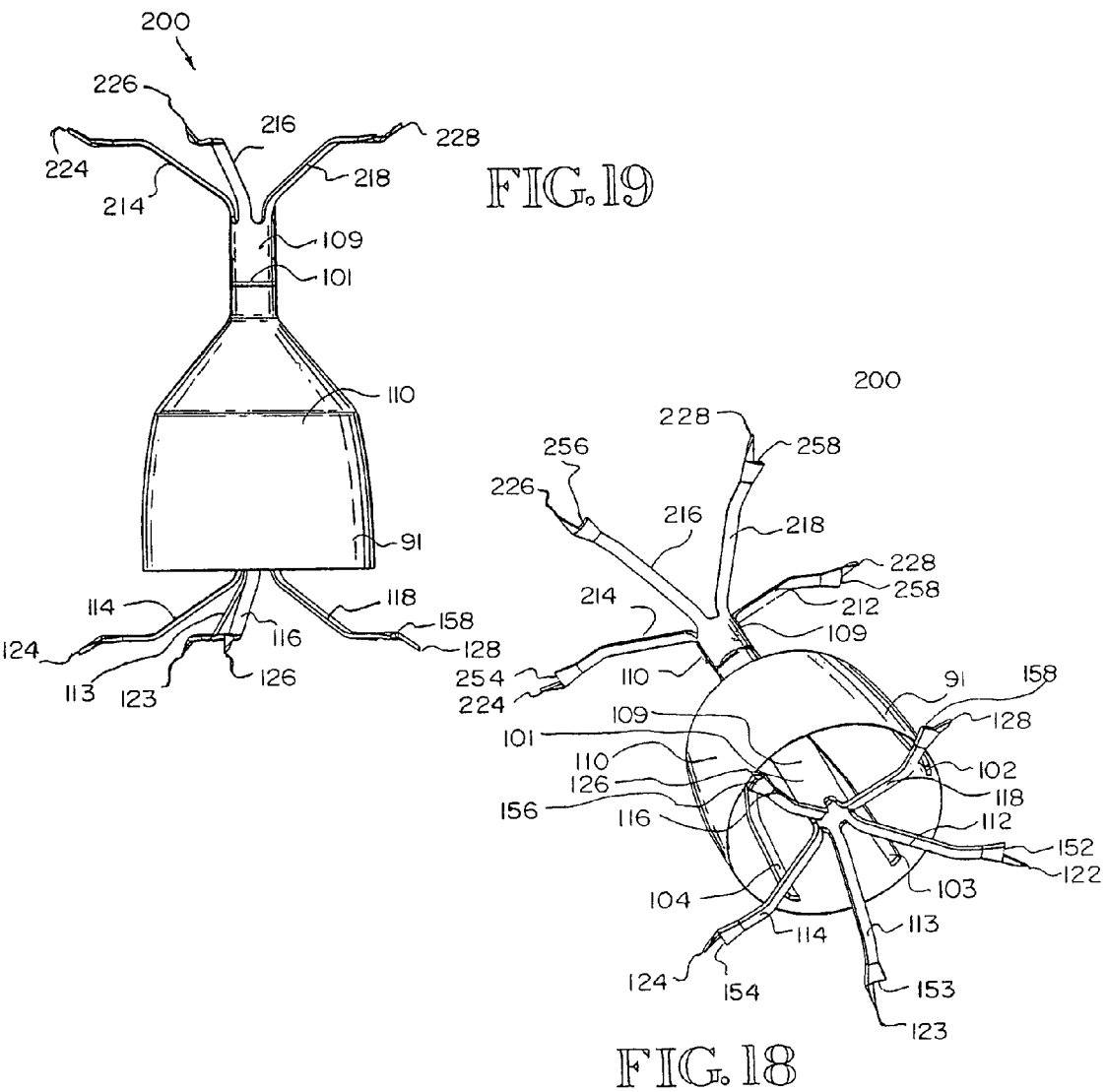

ONE-WAY VALVE DEVICES FOR ANCHORED IMPLANTATION IN A LUNG

CROSS REFERENCE TO RELATED APPLICATIONS

This is a continuation of U.S. patent application Ser. No. 10/150,547, filed on May 17, 2002, now abandoned the entire contents of which are incorporated herein by reference.

BACKGROUND

The present invention is generally directed to a removable anchored device, system, and method for treating Chronic Obstructive Pulmonary Disease (COPD). The present invention is more particularly directed to providing an anchored intra-bronchial obstruction that may be removable.

COPD has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991, COPD was the fourth leading cause of death in the United States and had increased 33% since 1979. COPD affects the patient's whole life. It has three main symptoms: cough; breathlessness; and wheeze. At first, breathlessness may be noticed when running for a bus, digging in the garden, or walking uphill. Later, it may be noticed when simply walking in the kitchen. Over time, it may occur with less and less effort until it is present all of the time. COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled beta-agonists. For those patients who respond poorly to the foregoing or who have persistent symptoms, ipratropium bromide may be indicated. Further, courses of steroids, such as corticosteroids, may be required. Lastly, antibiotics may be required to prevent infections and influenza and pneumococcal vaccines may be routinely administered. Unfortunately, there is no evidence that early, regular use of pharmacotherapy will alter the progression of COPD.

About 40 years ago, it was first postulated that the tethering force that tends to keep the intrathoracic airways open was lost in emphysema and that by surgically removing the most affected parts of the lungs, the force could be partially restored. Although the surgery was deemed promising, the lung volume reduction surgery (LVRS) procedure was abandoned. LVRS was later revived. In the early 1990's, hundreds of patients underwent the procedure. However, the procedure fell out of favor when Medicare stopped reimbursing for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life. Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

Lastly, lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

There is a need for additional non-surgical options for permanently treating COPD. A promising new therapy includes non-surgical apparatus and procedures for lung volume reduction by permanently obstructing the air passageway that communicates with the portion of the lung to be collapsed. The therapy includes placing an obstruction in the air passageway that prevents inhaled air from flowing into the portion of the lung to be collapsed. Lung volume reduction with concomitant improved pulmonary function may be obtained without the need for surgery. The effectiveness of obstructions may be enhanced if it is anchored in place. The effectiveness may also be enhanced if the obstruction is removable. However, no readily available apparatus and method exists for anchoring the obstruction, and for removal if required.

In view of the foregoing, there is a need in the art for a new and improved apparatus and method for permanently obstructing an air passageway that is anchored in place, and that may be removed if required. The present invention is directed to a device, system, and method that provide such an improved apparatus and method for treating COPD.

SUMMARY

The present invention provides an anchored intra-bronchial device for placement in an air passageway of a patient to collapse a lung portion associated with the air passageway. The device includes a support structure, an obstructing member carried by the support structure that prevents air from being inhaled into the lung portion to collapse the lung portion, and at least one anchor carried by the support structure that anchors the obstruction device within the air passageway when the anchor is deployed. The support structure, or a portion thereof, may be collapsible. The obstructing member and at least one anchor may be simultaneously deployable. The support structure may be configured to urge at least one anchor to engage the air passageway wall. The obstructing member may be a one-way valve. The obstructing member may be releasable from the support structure and removable from the air passageway.

In accordance with the present invention, alternative embodiments are provided for the anchors. An anchor may have an anchoring end that engages the air passageway wall, and that may pierce into the air passageway wall. An anchor may include a stop dimensioned for limiting the piercing of the air passageway wall. An anchor may include a resilient material for imparting a force against the air passageway to deform the air passageway to more positively anchor the obstructing member. An anchor may be releasable from the air passageway for removal of the intra-bronchial device. An anchor may include a pad that frictionally engages the air passageway. Further, an anchor may be configured to move from a first configuration to a second configuration to engage the air passageway. An anchor may be configured to move from a first configuration to a second configuration to engage the air passageway, and to move from the second configuration to the first configuration to disengage the air passageway. Alternatively, an anchor may be configured to move from a first configuration to a second configuration to engage the air passageway, and to move from the second configuration to a third configuration to disengage the air passageway.

In accordance with the present invention, alternative embodiments provide for the anchors to be carried on different portions of the device. An anchor may be carried by a peripheral portion of the support structure, and/or by a central portion of the support structure. An anchor may be carried distal to the obstructing member, and/or proximal to the obstructing member.

The present invention further provides a method of reducing the size of a lung, or reducing ventilation to a portion of a lung, by collapsing at least a portion of the lung. The method includes the step of providing an intra-bronchial device that includes a support structure, an obstructing member carried by the support structure which is so dimensioned when deployed in an air passageway communicating with the portion of the lung to be collapsed to preclude air from being inhaled, and at least one anchor carried by the support structure that anchors the obstructing member when the anchor is deployed. The method further includes the steps of placing the obstructing member in the air passageway, and deploying at least one anchor. An anchor may be releasable for removal of the intra-bronchial device. The obstructing member may form a one-way valve. The support structure may be collapsible.

The present invention yet further provides a method of reducing the size of a lung, or reducing ventilation to a portion of a lung, by collapsing a portion of the lung with a removable device. The method includes the step of providing an intra-bronchial device comprising a support structure, an obstructing member carried by the support structure which is so dimensioned when deployed in an air passageway communicating with the portion of the lung to be collapsed to preclude air from being inhaled, and at least one anchor carried by the support structure that anchors the obstructing member when the anchor is deployed. The method further includes the steps of placing the obstructing member in the air passageway, and deploying at least one anchor. The method further includes the step of removing at least the obstructing member. At least one anchor may be releasable from the air passageway for removal of at least the obstructing device, and the step of removing at least the obstructing device includes releasing at least one anchor. At least a portion of the obstructing member is releasable from the support structure, and the step of removing at least the obstructing member includes releasing the obstructing member from the support structure. The obstructing member may form a one-way valve. At least a portion of the support structure may be collapsible.

The present invention additionally provides an air passageway obstructing device. The device includes frame means for forming a support structure, flexible membrane means for obstructing air flow within the air passageway and carried by the support structure, and anchoring means to anchor the air passageway obstructing device, carried by the support structure. The frame means is expandable to an expanded state within an air passageway to support the membrane means and the anchoring means. The anchoring means is releasable for removal of the device from the air passageway.

These and various other features as well as advantages which characterize the present invention will be apparent from a reading of the following detailed description and a review of the associated drawings.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

FIG. 18 is a perspective view illustrating an alternative embodiment of a removable intra-bronchial device with both distal and proximal anchors carried on corresponding peripheral portions of the central support structure in accord with the present invention; and FIG. 19 is a side view of the device of FIG. 18.

DETAILED DESCRIPTION OF THE PREFERRED EMBODIMENTS

Figure 1:
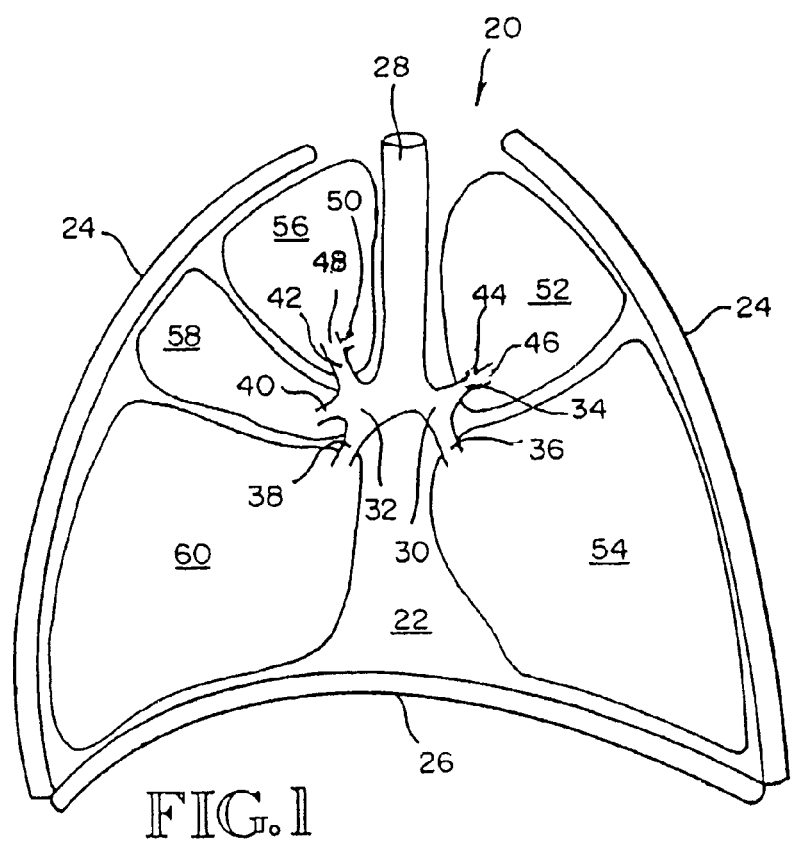
FIG. 1 is a simplified sectional view of a thorax illustrating a healthy respiratory system.

In the following detailed description of exemplary embodiments of the invention, reference is made to the accompanying drawings that form a part hereof. The detailed description and the drawings illustrate how specific exemplary embodiments by which the invention may be practiced. These embodiments are described in sufficient detail to enable those skilled in the art to practice the invention. It is understood that other embodiments may be utilized, and other changes may be made, without departing from the spirit or scope of the present invention. The following detailed description is therefore not to be taken in a limiting sense, and the scope of the present invention is defined by the appended claims.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

Additionally, throughout the specification, claims, and drawings, the term "proximal" means nearest the trachea, and "distal" means nearest the bronchioles.

Briefly stated, an aspect of the invention provides an anchored intra-bronchial device for placement in an air passageway of a patient. The intra-bronchial device obstructs the air passageway, reducing the ventilation to a portion of the lung and/or collapsing the lung portion associated with the air passageway. A further aspect of the invention provides removability of the intra-bronchial device, either by releasing the anchors for removal of the entire device or by separating the obstructing member and removing it.

FIG. 1 is a sectional view of a healthy respiratory system. The respiratory system 20 resides within the thorax 22 that occupies a space defined by the chest wall 24 and the diaphragm 26.

The respiratory system 20 includes the trachea 28, the left mainstem bronchus 30, the right mainstem bronchus 32, the bronchial branches 34, 36, 38, 40, and 42 and sub-branches 44, 46, 48, and 50. The respiratory system 20 further includes left lung lobes 52 and 54 and right lung lobes 56, 58, and 60. Each bronchial branch and sub-branch communicates with a respective different portion of a lung lobe, either the entire lung lobe or a portion thereof. As used herein, the term "air passageway" is meant to denote either a bronchi or bronchiole, and typically means a bronchial branch or sub-branch which communicates with a corresponding individual lung lobe or lung lobe portion to provide inhaled air thereto or conduct exhaled air therefrom.

Characteristic of a healthy respiratory system is the arched or inwardly arcuate diaphragm 26. As the individual inhales, the diaphragm 26 straightens to increase the volume of the thorax 22. This causes a negative pressure within the thorax. The negative pressure within the thorax in turn causes the lung lobes to fill with air. When the individual exhales, the diaphragm returns to its original arched condition to decrease the volume of the thorax. The decreased volume of the thorax causes a positive pressure within the thorax which in turn causes exhalation of the lung lobes.

Figure 2:
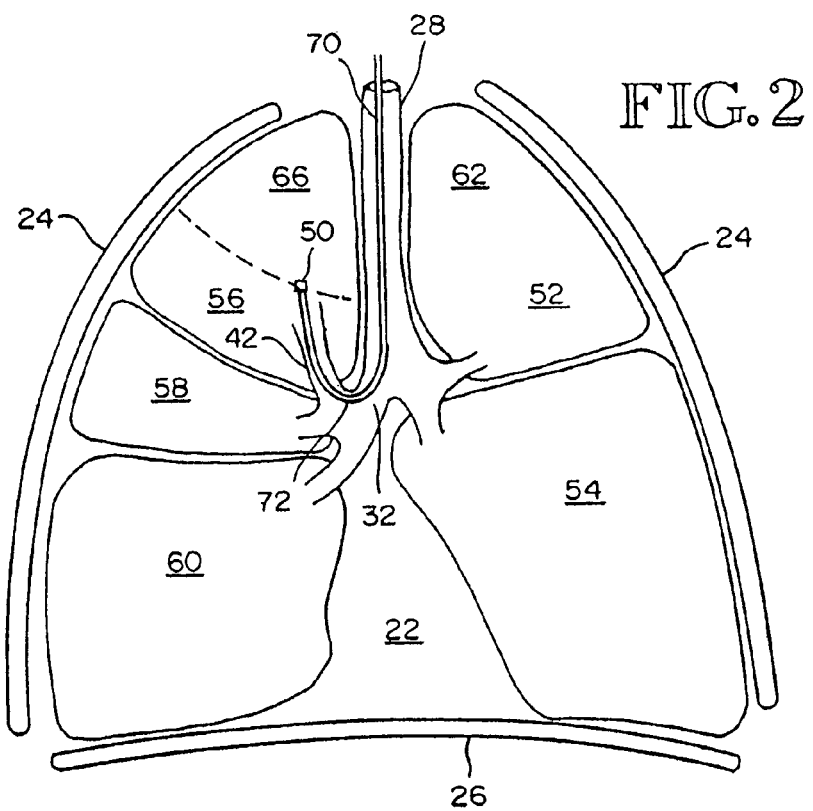
FIG. 2 is a sectional view similar to FIG. 1, but illustrating a respiratory system suffering from COPD and the execution of a first step in treating the COPD condition by reducing the size of a lung portion in accordance with the present invention.

In contrast to the healthy respiratory system of FIG. 1, FIG. 2 illustrates a respiratory system suffering from COPD. Here it may be seen that the lung lobes 52, 54, 56, 58, and 60 are enlarged and that the diaphragm 26 is not arched but substantially straight. Hence, this individual is incapable of breathing normally by moving diaphragm 26. Instead, in order to create the negative pressure in thorax 22 required for breathing, this individual must move the chest wall outwardly to increase the volume of the thorax. This results in inefficient breathing causing these individuals to breathe rapidly with shallow breaths.

It has been found that the apex portions 62 and 66 of the upper lung lobes 52 and 56, respectively, are most affected by COPD. Hence, bronchial sub-branch obstructing devices are generally employed for treating the apex 66 of the right, upper lung lobe 56. However, as will be appreciated by those skilled in the art, the present invention may be applied to any lung portion without departing from the present invention. As will be further appreciated by those skilled the in art, the present invention may be used with any type of obstructing member to provide an anchored obstructing device, which may be removed. The inventions disclosed and claimed in U.S. Pat. Nos. 6,258,100 and 6,293,951, both of which are incorporated herein by reference, provide an improved therapy for treating COPD by obstructing an air passageway using an intra-bronchial valve or plug. The present invention may be used with the apparatus, system, and methods of these patents as will be briefly described in conjunction with the disclosure of the preferred embodiments of the present invention.

The insertion of an obstructing member treats COPD by deriving the benefits of lung volume reduction surgery without the need of performing the surgery. The treatment contemplates permanent collapse of a lung portion. This leaves extra volume within the thorax for the diaphragm to assume its arched state for acting upon the remaining healthier lung tissue. As previously mentioned, this should result in improved pulmonary function due to enhanced elastic recoil, correction of ventilation/perfusion mismatch, improved efficiency of respiratory musculature, and improved right ventricle filling. The present invention supports the use of intra-bronchial obstructions to treat COPD by anchoring the obstruction device in the air passageway. The present invention further supports the use of intra-bronchial obstructions by providing for their removal if necessary. Use of anchors can allow the obstructing member to be relatively loosely fitted against the air passageway wall, which may preserve mucociliary transport of mucus and debris out of the collapsed lung portion and allow distal mucus to be coughed.

FIG. 2 also illustrates a step in COPD treatment using an obstructing member. Treatment is initiated by feeding a conduit or catheter 70 down the trachea 28, into the right mainstem bronchus 32, into the bronchial branch 42 and into and terminating within the sub-branch 50. The sub-branch 50 is the air passageway that communicates with the lung portion 66 to be treated, and is also referred to herein as air passageway 50. The catheter 70 is preferably formed of flexible material such as polyethylene. Also, the catheter 70 is preferably preformed with a bend 72 to assist the feeding of the catheter from the right mainstem bronchus 32 into the bronchial branch 42.

Figure 3:
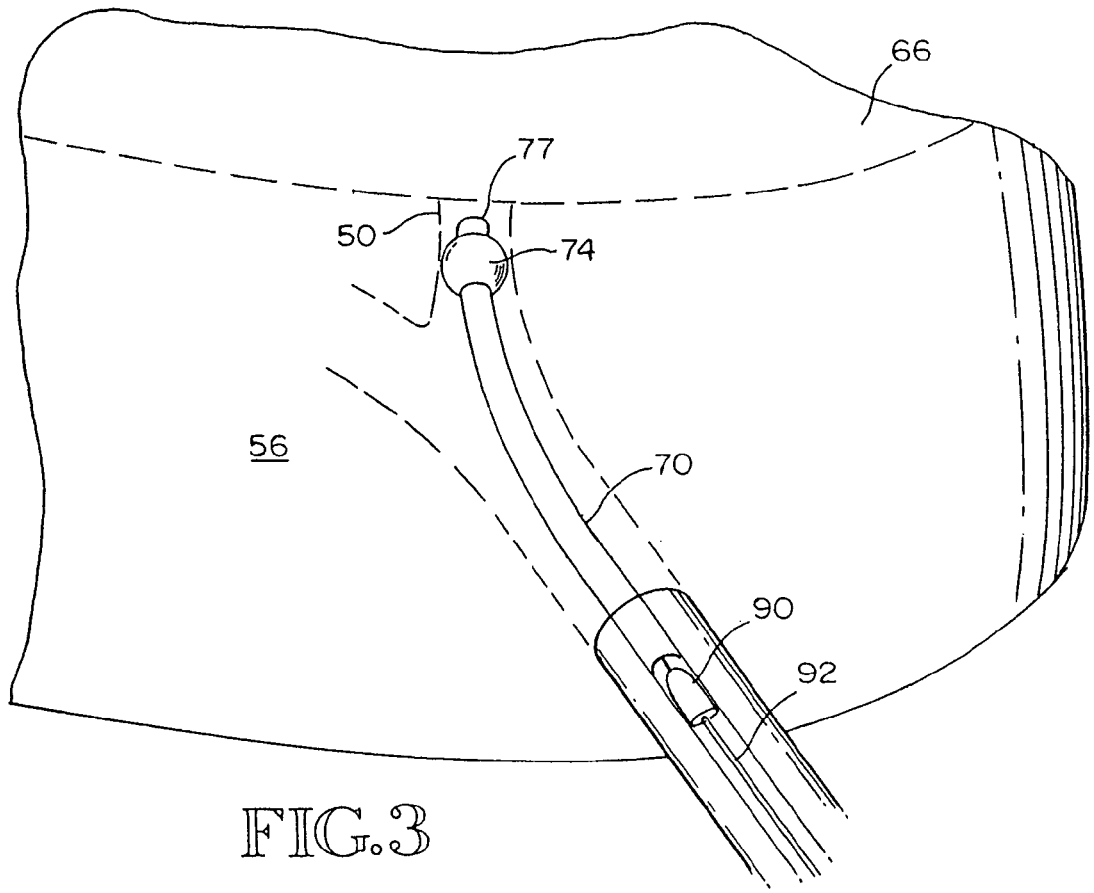
FIG. 3 is perspective view, partially in section, and to an enlarged scale, illustrating an intermediate step in the treatment.

FIG. 3 illustrates a further step in a method for placing an obstructing member 90 in a bronchial sub-branch using a catheter. The invention disclosed herein is not limited to use with the particular method illustrated herein. Catheter 70 includes an optional inflatable sealing member 74 for use with a vacuum to collapse lung portion 66 prior to insertion of obstructing member 90. The obstructing member 90 may be formed of resilient or collapsible material to enable the obstructing member 90 to be fed through the conduit 70 in a collapsed state. The stylet 92 is used to push the obstructing member 90 to the end 77 of the catheter 70 for placing the obstructing member 90 within the air passageway 50 adjacent to the lung portion 66 to be permanently collapsed. Optional sealing member 74 is withdrawn after obstructing member 90 is inserted.

Another step in placing an obstructing member 90 may include sizing the air passageway location where the obstructing member 90 will be positioned.

A function of the intra-bronchial device disclosed and claimed in this specification, including the detailed description and the claims, is described in terms of collapsing a lung portion associated with an air passageway. In some lungs, a portion of a lung may receive air from collateral air passageways. Obstructing one of the collateral air passageways may reduce the volume of the lung portion associated with the air passageway, but not completely collapse the lung portion, as that term may be generally understood. As used herein, the meaning of "collapse" includes both a complete collapse of a lung portion, and a partial collapse resulting in a marked decrease in the volume of a lung portion.

Once deployed, the obstructing member precludes inhaled air from entering the lung portion to be collapsed. In accordance with the present invention, it is preferable that the obstructing member takes the form of a one-way valve. In addition to precluding inhaled air from entering the lung portion, the member further allows air within the lung portion to be exhaled. This results in more rapid collapse of the lung portion. In addition, anchoring obstructing members that preclude both inhaled and exhaled airflow are contemplated as within the scope of the invention.

Figure 4:
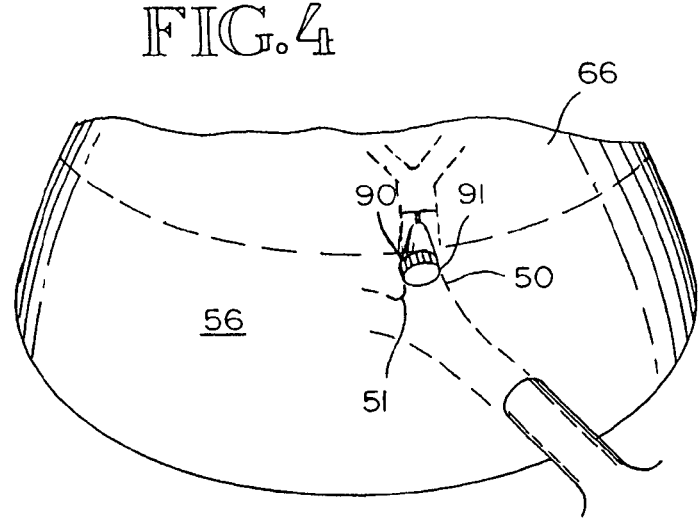
FIG. 4 is a perspective view of a conduit that may be utilized in practicing the present invention.

FIG. 4 illustrates the obstructing device in place within air passageway 50. Obstructing member 90 has expanded upon placement in the air passageway 50 to seal the air passageway 50. This causes the lung portion 66 to be maintained in a permanently collapsed state. The obstructing member 90 may be any shape suitable for accomplishing its purpose, and may be a solid material or a membrane.

More specifically, the obstructing member 90 has an outer dimension 91, and when expanded, enables a contact zone with the air passageway inner dimension 51. This seals the air passageway upon placement of the obstructing member 90 in the air passageway 50 for maintaining the lung portion 66 in the collapsed state.

Alternatively, the lung portion 66 may be collapsed using vacuum prior to placement of obstructing member 90, or sealing the air passageway 50 with obstructing member 90 may collapse it. The air within the lung portion 66 will be absorbed by the body over time, reducing the volume of and/or collapsing the lung portion 66. Alternatively, obstructing member 90 may include the function of a one-way valve that allows air to escape from lung portion 66. Lung portion 66 will then collapse, and the valve will prevent air from being inhaled.

Figure 5:
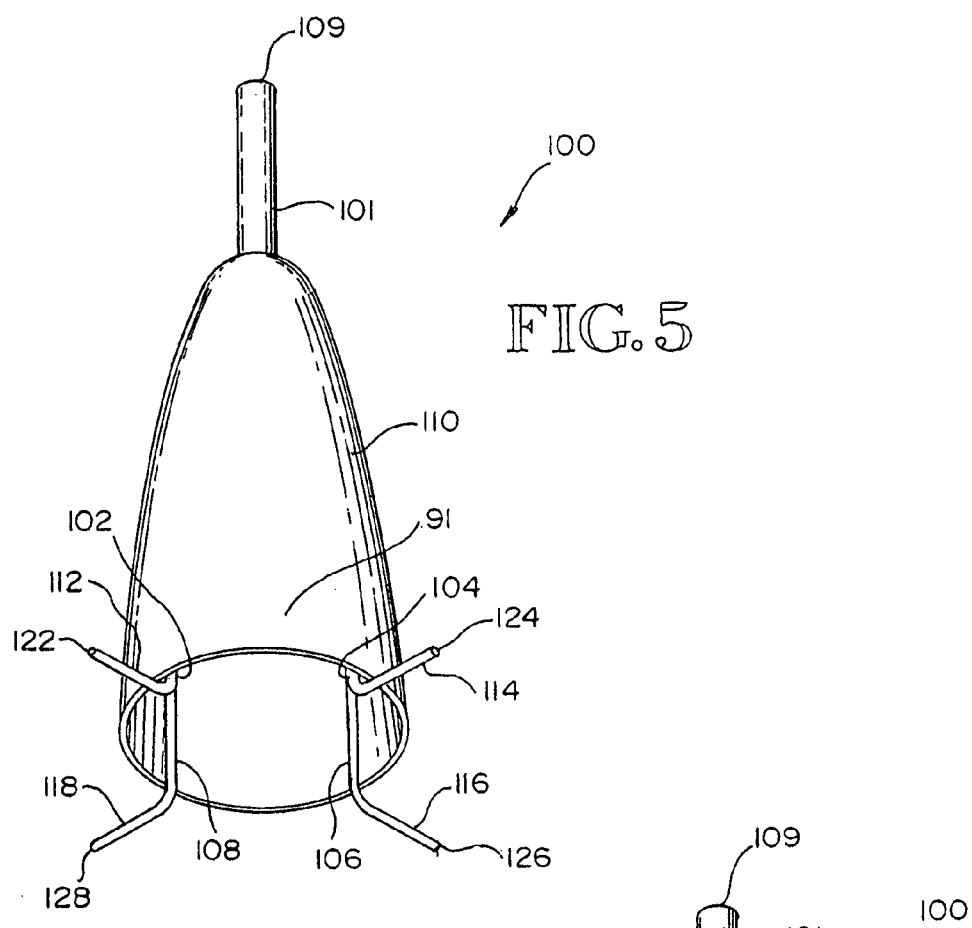
FIG. 5 is a perspective view of an intra-bronchial device, with anchors located proximally on peripheral portions of the support members, as the device would appear when fully deployed in an air passageway in accordance with the present invention.

FIG. 5 is a perspective view of an intra-bronchial device, with anchors located proximally on peripheral portions of the support members, as the device would appear when fully deployed in an air passageway in accordance with the present invention. Intra-bronchial device 100 includes a support structure 101, a central support structure 109; support members 102, 104, 106, and 108; anchors 112, 114, 116, and 118; anchor ends 122, 124, 126, and 128; and an obstructing member 110.

The support structure 101 of intra-bronchial device includes central support structure 109, and support members 102, 104, 106, and 108. The support members 102, 104, 106, and 108, carry anchors 112, 114, 116, and 118; and anchor ends 122, 124, 126, and 128, respectively. Central support structure 109 is a tubular member, preferably hypodermic needle tubing. Support members 102, 104, 106, and 108, are coupled mechanically to central support structure 109, such as by crimping, or by other methods such as adhesive or welding. Support members 102, 104, 106, and 108 are generally similar to each other. The support members are preferably formed of stainless steel, Nitinol, or other suitable material having a memory of its original shape, and resiliency to return the material to that shape.

Anchors 112, 114, 116, and 118 are extensions of support members 102, 104, 106, and 108. The anchors are formed by bending the support members to an angle that will result in a deployed anchor engaging the air passageway wall by piercing it approximately perpendicularly. In this preferred embodiment, the bend angle is approximately a right angle. Anchor ends 122, 124, 126, and 128 may be shaped to promote piercing the air passageway wall. In an alternative embodiment, the elements of support structure 101 may be formed by laser cutting a single piece of hypodermic needle tubing.

Obstructing member 110 is carried on the support structure 101, and includes a flexible membrane open in the proximal direction and which may be formed of silicone or polyurethane, for example. The obstructing member 110 is secured to the central support structure 109, and may be additionally secured to the support members at its larger diameter 91. It may be secured by adhesive, or other manner known in the art. Obstructing member 110 may be loosely carried on support members 102, 104, 106, and 108, such that it expands on inhalation to form a seal against a wall of the air passageway, and contracts on exhalation to allow air and mucociliary transport from the collapsed lung. This provides a one-way valve function.

Figure 6:
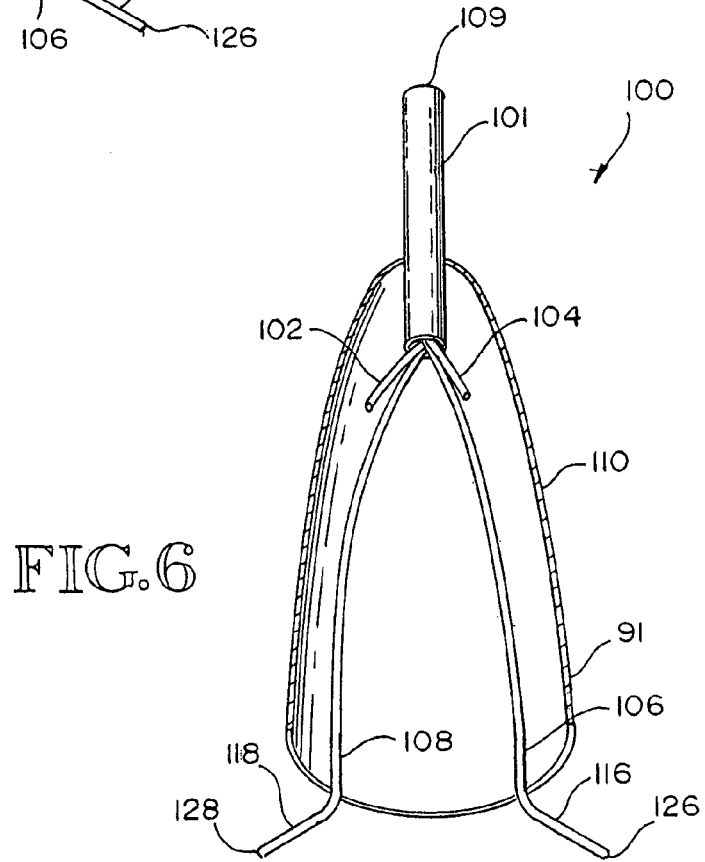
FIG. 6 is a partial section view of the device of FIG. 5 showing additional details of the support structure.

FIG. 6 is a partial section view of the device of FIG. 5 showing additional detail of the support structure. The linear cross-section view of FIG. 6 exposes the arrangement of support members 106 and 108 in their deployed configuration. The details of support members 102 and 104 are omitted from FIG. 6 for clarity, but are the same as support members 106 and 108. The distal end of obstructing member 110 is carried on central support structure 109. Support members 106 and 108 are shown emanating from central support structure 109, and arranged to loosely support to obstructing member 110 at its larger diameter 91. This allows obstructing member 110 to expand on inhalation and seal at the contact zone (element 129 of FIG. 7), and to partially contract on exhalation to allow exhalation of air and mucociliary transport. In an alternative embodiment, support members 106 and 108 do not actively support obstructing member 110, and the expansion and contraction of obstructing member 110 is governed by its elasticity.

Figure 7:
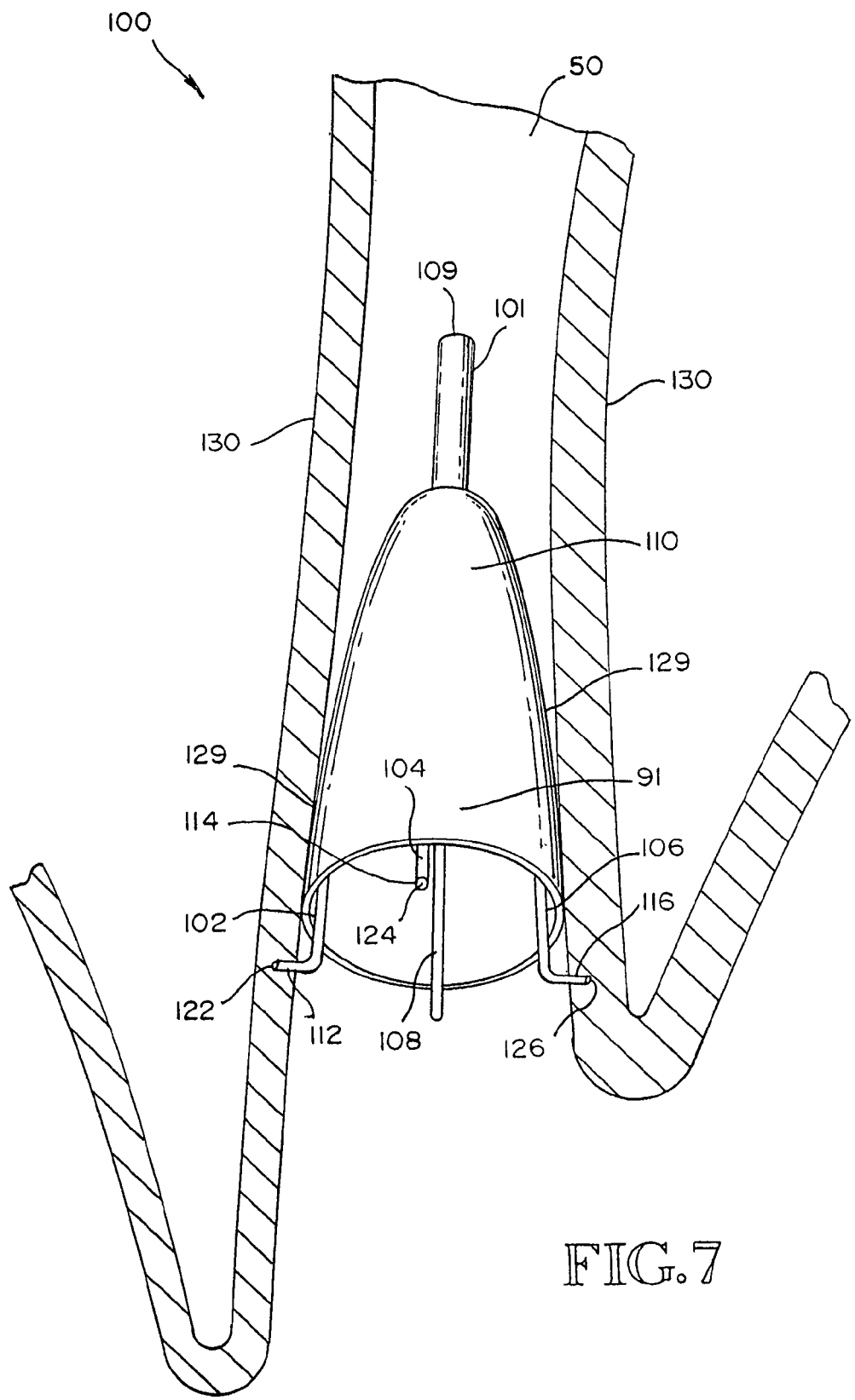
FIG. 7 is a perspective view of the intra-bronchial device of FIG. 5 anchored in an air passageway.

FIG. 7 is a perspective view of the intra-bronchial device of FIG. 5 anchored in an air passageway. Intra-bronchial device 100 is illustrated with anchors 112 and 116 piercing into the air passageway wall 130 of air passageway 50. This anchors the intra-bronchial device 100 in place.

Intra-bronchial device 100 is collapsible for insertion into an internal lumen of a catheter. At least the support members 102, 104, 106, and 108, and the obstructing member 110, may be collapsed. Intra-bronchial device 100 is inserted into the catheter lumen, which is typically already placed in the air passageway 50 as generally illustrated in FIG. 3. Using the stylet, intra-bronchial device 100 is advanced down the catheter lumen into the air passageway 50 to where the device is to be deployed. Once the point of deployment is reached, intra-bronchial device 100 is expelled from the catheter and assumes its deployed shape as illustrated in FIG. 5. Upon deployment, obstructing member 110 forms a contact zone 129 with the wall 130 of the air passageway 50 to prevent air from being inhaled into the lung portion to collapse the lung portion. Simultaneously upon deployment, the memory and resiliency of the support members 102, 104, 106, and 108 impart a force on the anchor ends 122, 124, 126, and 128, and urge the anchors 112, 114, 116, and 118 to engage air passageway wall 130 by piercing. The anchors pierce into and become embedded in the wall 130 of the air passageway 50, preferably without projecting through the wall 130. Stops may be incorporated into the anchors to limit piercing of the wall 130. For example, the bend between the support member and the anchor may form a stop.

The preclusion of air from being inhaled into the lung portion may be terminated by eliminating the obstructing effect of intra-bronchial device 100. The preclusion of air by the embodiment illustrated in FIGS. 5-7 may be eliminated by releasing anchors 112, 114, 116, and 118 from the air passageway wall 130. The anchors may be released by inserting a catheter into air passageway 50 in proximity to intra-bronchial device 100. A retractor device, such as biopsy forceps, capable of gripping a portion of intra-bronchial device 100 is inserted in the catheter. The forceps are used to engage a portion of the support structure 101 of intra-bronchial device 100, such as a support member or an anchor, or the obstructing member 110, and draw it toward the catheter. The drawing action releases anchors 112, 114, 116, and 118 from air passageway wall 130. The intra-bronchial device 110 is then drawn into the catheter with the forceps, causing the support structure 101 and obstructing member 110 to collapse. The collapsed device 100 now fully enters the catheter lumen for removal from the patient. Alternatively, the obstructing effect may be eliminated by grabbing the obstructing member 110, releasing it from the support structure 101, and removing obstructing member 110 from the patient.

Figure 8:
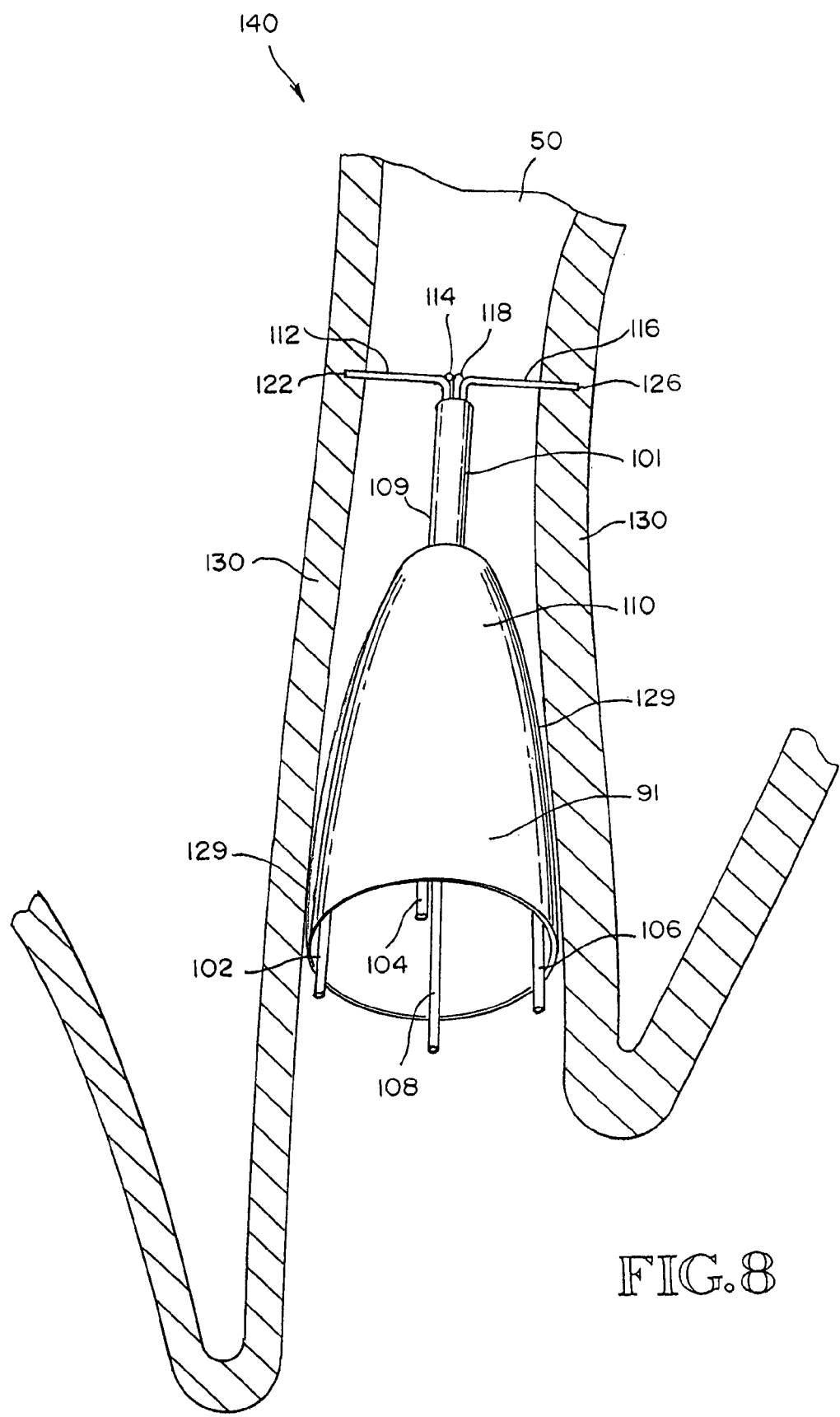
FIG. 8 illustrates an intra-bronchial device, with anchors carried distally on the central support structure, fully deployed in an air passageway in accordance with an alternative embodiment of the invention.

FIG. 8 illustrates an intra-bronchial device, with anchors carried distally on the central support structure, fully deployed in an air passageway in accordance with an alternative embodiment of the invention. The anchors 112, 114, 116, and 118 of intra-bronchial device 140 are carried on portions of support members 102, 104, 106, and 108 distal of the central support structure 109. The support members are gathered together and carried by the central support structure 109. Other than the anchors 112, 114, 116, and 118 being formed and carried on distal portions of support members 102, 104, 106, and 108, intra-bronchial device 140 is substantially similar in construction, operation, and removal as the intra-bronchial device 100 of FIG. 5.

When intra-bronchial device 140 is compressed for insertion into the catheter lumen for placement in the air passageway, the anchors 112, 114, 116, and 118 are collapsed into a first configuration. In the first configuration, the anchor ends 122, 124, 126, and 128 are moved toward obstructing member 110, and anchors 112, 114, 116, and 118 thereby folded toward obstructing member 110. In an alternative embodiment, the anchor ends 122, 124, 126, and 128 are moved away from obstructing member 110, and anchors 112, 114, 116, and 118 thereby folded away from obstructing member 110.

When intra-bronchial device 100 is deployed from the catheter lumen, the memory and resiliency of the anchors 112, 114, 116, and 118 impart a force that moves the anchor ends 122, 124, 126, and 128 into a second configuration to engage air passageway wall 130. This is the deployed configuration illustrated in FIG. 8. For removal, drawing intra-bronchial device 140 toward the catheter causes the anchor ends 122, 124, 126, and 128 to move away from obstructing member 110 to a third configuration. Anchors 112, 114, 116, and 118 are thereby folded away from obstructing member 110 and are released from engagement with air passageway wall 130 for removal of the intra-bronchial device 140. In an alternative embodiment, the anchors 112, 114, 116, and 118 may be formed on additional support members carried by central support structure 109, instead of being formed from distal portions of support members 102, 104, 106, and 108.

Figure 9:
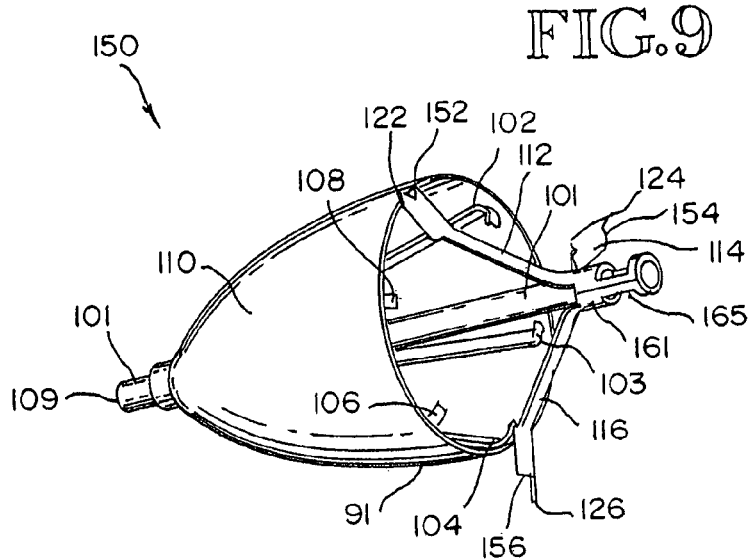
FIG. 9 is a perspective view of an intra-bronchial device, with proximal anchors carried on the central support structure, in accordance with an alternative embodiment of the invention.
Figure 10:
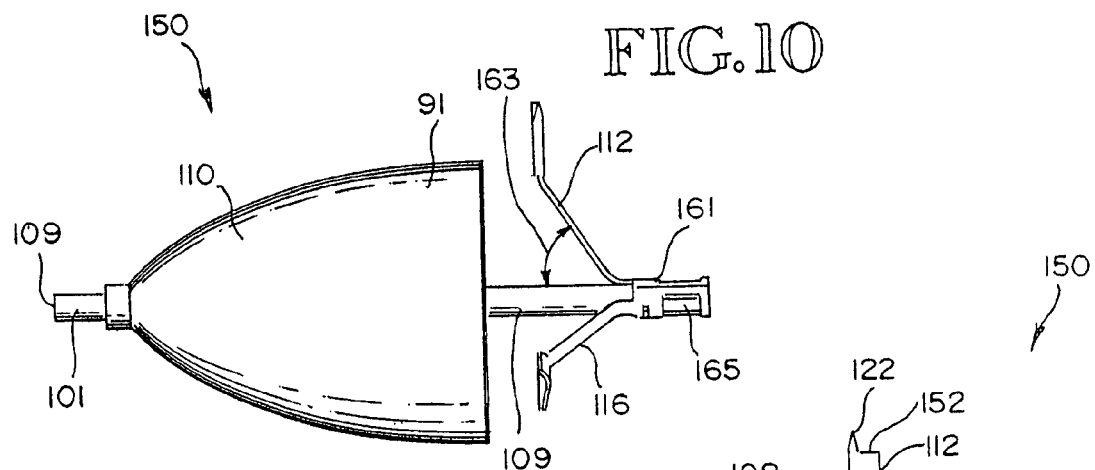
FIG. 10 is a side view of an intra-bronchial device, with proximal anchors carried on the central support structure, in accordance with an alternative embodiment of the invention.
Figure 11:
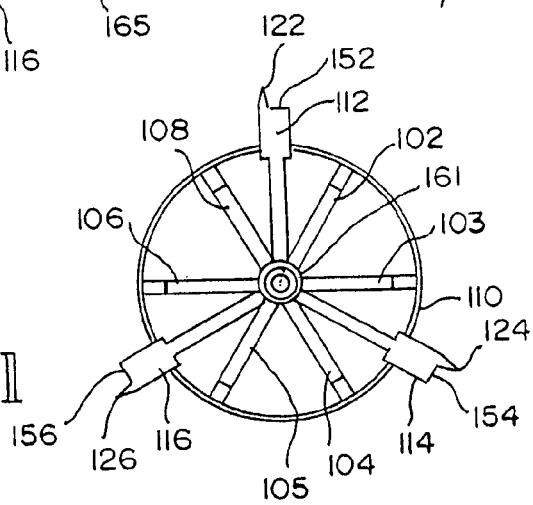
FIG. 11 is an end view of an intra-bronchial device, with proximal anchors carried on the central support structure, in accordance with an alternative embodiment of the invention.

FIGS. 9-11 illustrate an intra-bronchial device, with proximal anchors carried on the central support structure, in accordance with an alternative embodiment of the invention. FIG. 9 is a perspective view, FIG. 10 is a side view, and FIG. 11 is an end view of the device. Intra-bronchial device 150 is generally similar in construction, operation, placement, and removal to the intra-bronchial device 100 of FIG. 5. Its structure has six support members and three anchors, with anchor stops. Anchors 112, 114, and 116 include stops 152, 154, and 156 respectively. Intra-bronchial device 150 also includes an anchor base 161, an anchor base aperture 165, anchor base angle 163, and two additional support members 103 and 105.

Central support structure 109 extends both proximal and distal of obstructing member 110, and carries anchor base 161 proximal of obstructing member 110, carries anchors 112, 114, and 116, and includes anchor base aperture 165. The linear plane of anchors 112, 114, and 116 intersect anchor base 161 at anchor base angle 163. Anchor base angle 163 is selected to optimize anchor deployment force and anchor release. Stops 152, 154, and 156 include a flat area to limit the piercing of the air passageway wall by anchor ends 122, 124, and 126. In alternative embodiments, the stops can be any configuration or shape known to those skilled in the art to limit the piercing.

In operation, when intra-bronchial device 150 is compressed for insertion into the catheter lumen for placement in the air passageway, anchors 112, 114, and 116 are collapsed into a first configuration. In the first configuration, the anchor ends 122, 124, and 126 are moved toward obstructing member 110, thereby decreasing anchor base angle 163 and folding anchors 112, 114, and 116 toward obstructing member 110. The anchor ends and the anchors may be moved by sliding a catheter or hollow member over anchor base 161 and toward obstructing member 110. When intra-bronchial device 150 is deployed from the catheter lumen, the memory and resiliency of the anchors 112, 114, and 116, anchor angle 163, and anchor base 161 impart a force that moves the anchor members into a second configuration, which is the deployed configuration, to engage air passageway wall 130. The second or deployed configuration is illustrated in FIGS. 9-11. Stops 152, 154, and 156 limit the piercing of the air passageway wall by anchor ends 122, 124, and 126.

For removal, a retractor device is deployed from a catheter to engage anchor base 161 and restrain intra-bronchial device 150. Anchor base aperture 165 is arranged for being gripped by a retractor device. The retractor device may be a biopsy forceps to engage anchor base 161, or a hooked device to engage anchor base aperture 165. The retractor device is then used to draw intra-bronchial device 150 proximal, releasing the anchors 112, 114, and 116 from the air passageway wall. This collapses the anchors into to the first configuration for removal.

In an alternative step to collapse the anchors, after anchor base 161 or aperture 165 is engaged, a catheter may then moved distally over anchor base 161, and in contact with anchors 112, 114, and 116. The catheter is further moved against anchors 112, 114, and 116, while intra-bronchial device 150 is restrained at anchor base 161. This releases the anchors 112, 114, and 116 from the air passageway wall. This collapses the anchors into to the first configuration for removal.

Continuing with the removal steps, intra-bronchial device 150 is then further drawn into the catheter by pulling on the retractor device used to engage anchor base 161. This collapses support structure 101 and obstructing member 110 so that they may be fully drawn into the catheter. Once drawn into the catheter, intra-bronchial device 160 may be removed from the air passageway and the patient.

Figure 12:
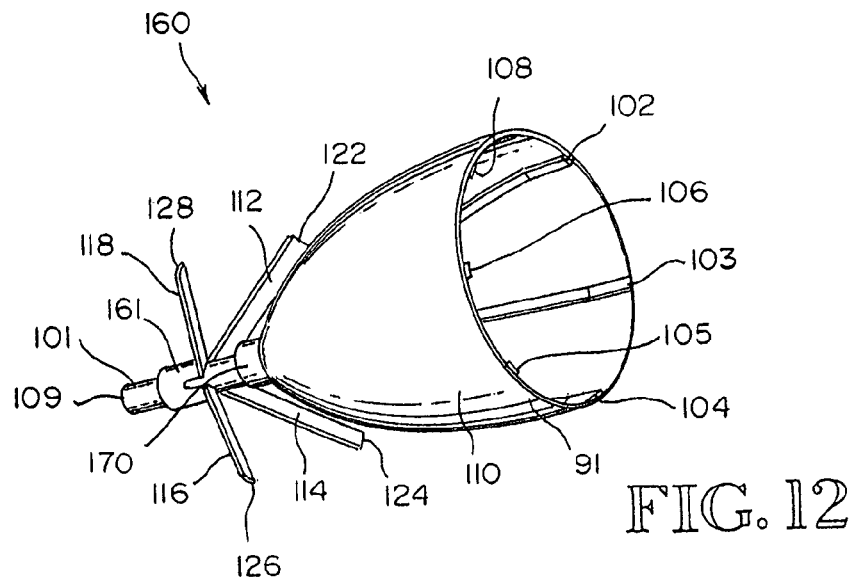
FIG. 12 is a perspective view of an intra-bronchial device, with distal friction anchors carried on the central support structure, in accordance with an alternative embodiment of the invention.
Figure 13:
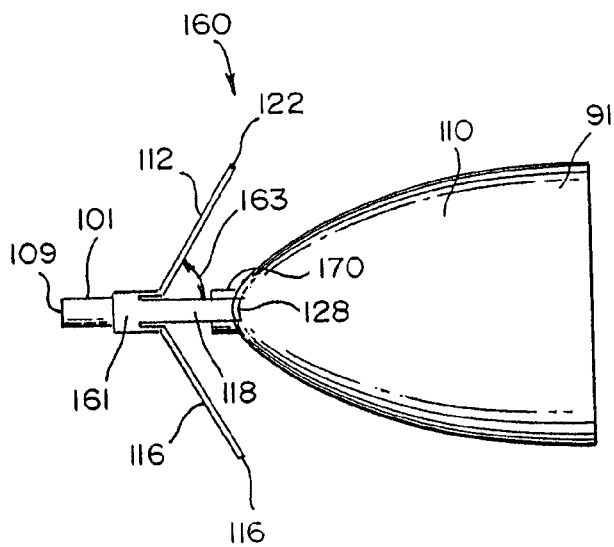
FIG. 13 is a side view of an intra-bronchial device, with distal friction anchors carried on the central support structure, in accordance with an alternative embodiment of the invention.
Figure 14:
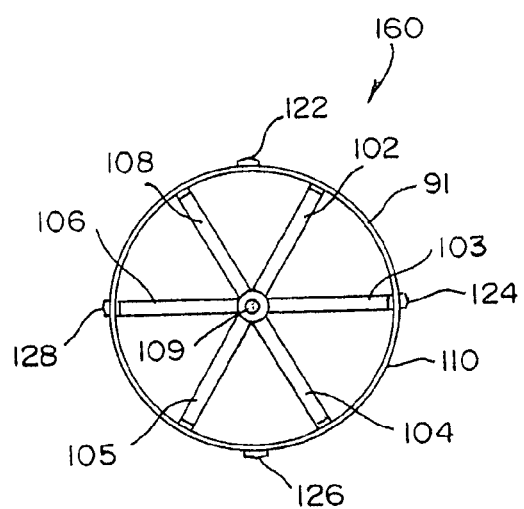
FIG. 14 is an end view of an intra-bronchial device, with distal friction anchors carried on the central support structure, in accordance with an alternative embodiment of the invention.

FIGS. 12-14 illustrate an intra-bronchial device, with distal friction anchors carried on the central support structure, in accordance with an alternative embodiment of the invention. FIG. 12 is a perspective view, FIG. 13 is a side view, and FIG. 14 is an end view. Intra-bronchial device 160 is generally similar in construction, placement, and operation to the intra-bronchial device 150 of FIGS. 9-11. Intra-bronchial device 160 is removed in the manner described in conjunction with FIG. 7. However, Intra-bronchial device 160 differs from intra-bronchial device 150 in that the structure includes four distal anchors with anchor ends 122, 124, 126, and 128 shaped into pads that deform and frictionally engage the air passageway wall to more positively anchor intra-bronchial device 160 without piercing. The structure also includes an obstructing member support base 170.

Central support structure 109 extends distal of obstructing member 110, and carries anchor base 161 distal of obstructing member 110. Anchor base 161 carries anchors 112, 114, 116, and 118. The linear plane of anchors 112, 114, 116, and 118 intersects anchor base 161 at anchor angle 163. Anchor angle 163 is selected to optimize anchor deployment force and anchor release. The anchors 112, 114, 116, and 118, and anchor base 161 may be constructed by laser cutting a single piece of hypodermic tubing lengthwise to form the anchors 112, 114, 116, and 118, and then bending the anchors to form anchor angle 163. Anchor base 161 is secured to central support structure 109. Support members 102, 103, 104, 105, 106, and 108, and the obstructing member support member base 170 may be constructed in a like manner. Obstructing member 110 is secured to the obstructing member support base 170, and alternatively to support members 102, 103, 104, 105, 106, and 108. The assembly of obstructing member 110 and support base 170 is secured to central support structure 109. Central support structure 109 may extend proximal of support member base 170 to provide a surface for gripping the intra-bronchial device 160 for removal, and may include an aperture to be engaged by a hooked device.

Figure 15:
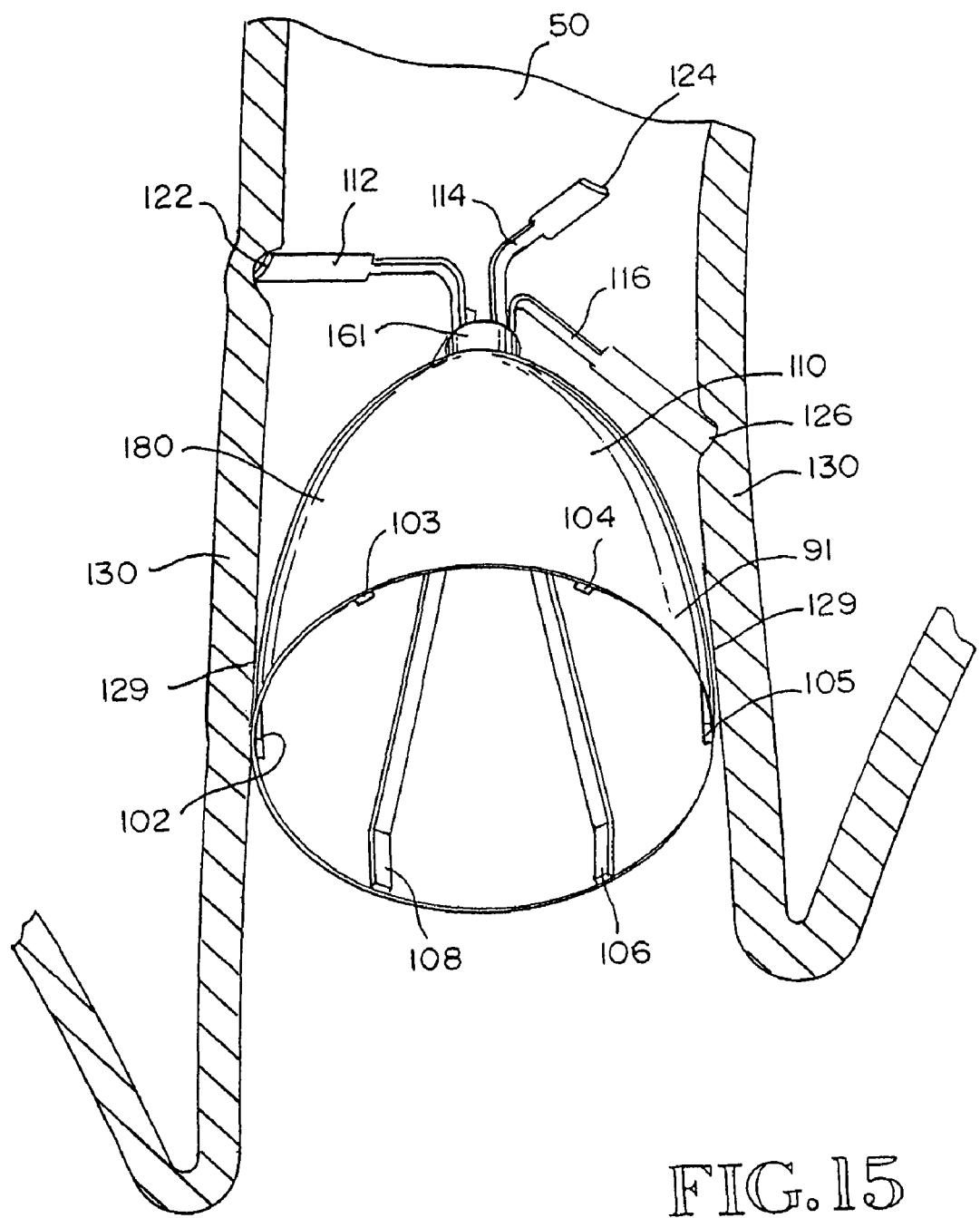
FIG. 15 is a perspective view of an intra-bronchial device similar to that of FIGS. 12-14 anchored in an air passageway.

FIG. 15 is a perspective view of an intra-bronchial device similar to that of FIGS. 12-14 anchored in an air passageway. It illustrates pad-shaped anchor ends 122-128 of intra-bronchial device 180 deforming and frictionally engaging air passageway wall 130.

Figure 16:
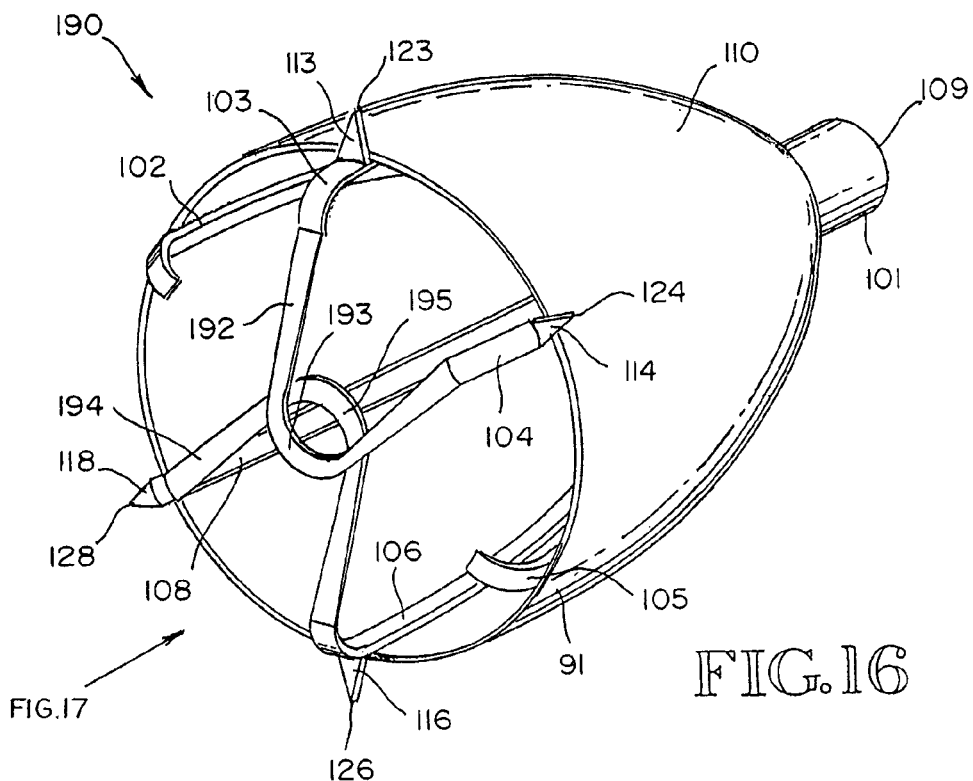
FIG. 16 is a perspective view illustrating an alternative embodiment of a removable intra-bronchial device with proximal anchors carried on a peripheral portion of a plurality of support structure members in accord with the present invention.
Figure 17:
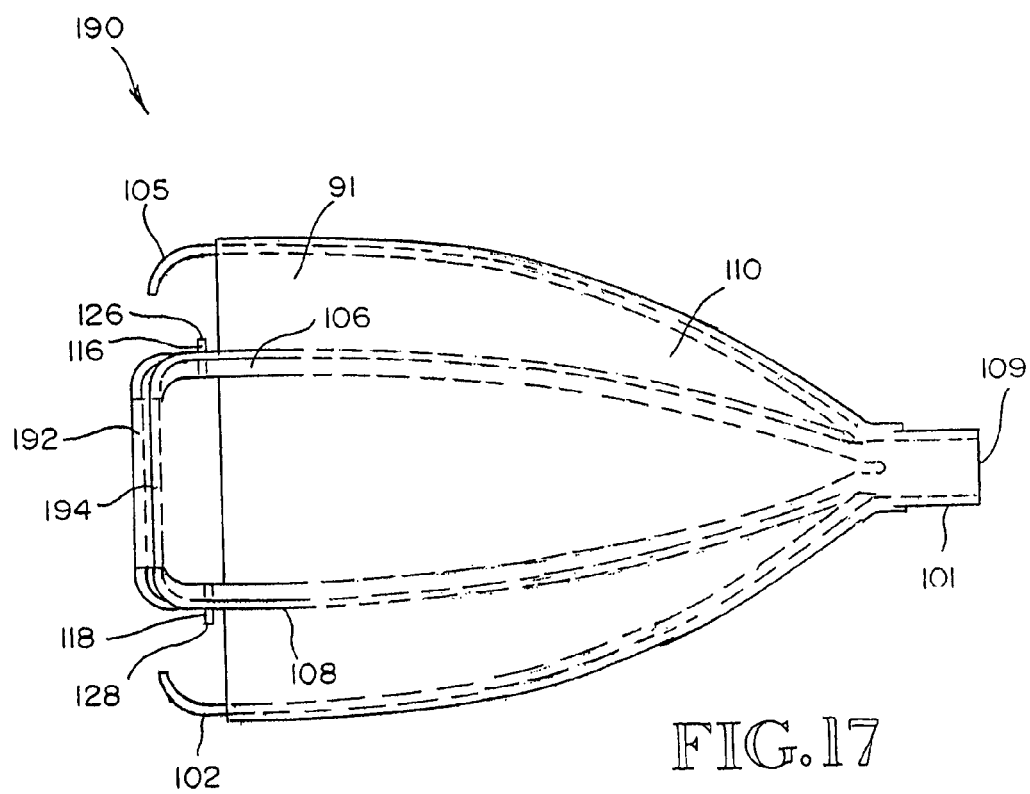
FIG. 17 is a side view of the device of FIG. 16.

FIGS. 16 and 17 illustrate a removable intra-bronchial device with proximal anchors carried on a peripheral portion of a plurality of support structure members in accord with the present invention. FIG. 16 is a perspective view, as the device would appear when fully deployed in an air passageway. FIG. 17 is a side view of FIG. 16. In a preferred embodiment, the support structure 101 of intra-bronchial device 190 includes six support members, with two opposing pairs of support members carrying anchors and each member of a pair being joined together by a retracting member. Intra-bronchial device 190 includes a support structure 101 having a central support structure 109 and support members 102, 103, 104, 105, 106, and 108; four anchors 113, 114, 116, and 118 having anchor ends 123, 124, 126, and 128 respectively; two "U" shaped retracting members 192 and 194 having an apex 193 and 195 respectively; and obstructing member 110.

Intra-bronchial device 190 is generally similar in construction, operation, placement, and removal to the intra-bronchial device 150 of FIG. 9. Support structure 101 is a tubular member, preferably hypodermic needle tubing, or stainless steel, Nitinol, or other suitable material having a memory of its original shape and resiliency to return the material to that shape. Support members 102, 103, 104, 105, 106, and 108, and central support structure 109 may be formed by laser cutting a single piece of hypodermic needle tubing lengthwise, and bending the support members to a required shape. Support members 102, 103, 104, 105, 106, and 108 are generally similar to each other. Anchors 113, 114, 116, and 118 are disposed on support members 103, 104, 106, and 108, respectively, in any manner available in the art. Anchors 113-118 are disposed on support members 103, 104, 106, and 108 to be located proximally of obstructing member 110, and to engage an air passageway wall when intra-bronchial device 190 is deployed.

"U" shaped retracting member 192 is coupled to support members 103 and 104, and "U" shaped retracting member 194 is coupled to support members 106 and 108. "U" shaped retracting members 192 and 194 may be constructed of any material suitable for use within a patient, and may or may not be resilient as required by the particular embodiment. When intra-bronchial device 190 is fully deployed in an air passageway, the "U" shaped retracting members 192 and 194 are arranged opposite each other, and they partially overlap, with the apex of one lying within a space bounded by the "U" shape of the other member. In the deployed configuration, increasing the distance between apex 193 and apex 195 moves support member pairs 103-104 and 106-108 centrally.

In operation, when intra-bronchial device 190 is compressed for insertion into a catheter lumen and placement in an air passageway, support members 102, 103, 104, 105, 106, and 108 are collapsed centrally into a first configuration. This causes the anchor ends 123, 124, 126 and 128 to move centrally.

When intra-bronchial device 190 is deployed from the catheter lumen, the memory and resiliency of the support member pairs 103,104 and 106,108 impart a force that moves the anchors 113 and 114, and 116 and 118, and their anchor ends 123 and 124, and 126 and 128 into a second configuration, which is the deployed configuration to engage air passageway wall. In addition, deployment of intra-bronchial device 190 may include a step of forcibly decreasing the distance between apexes 193 and 195 to forcibly move the anchors 113 and 114, and 116 and 118 into engagement with the wall of the air passageway. While the anchors 113 and 114, and 116 and 118 of this embodiment do not include stops, the expansive or peripheral movement of the anchors will be limited by the interior surface of obstructing member 110. This may limit the piercing of the air passageway wall by anchors 113 and 114, and 116 and 118.

In an alternative embodiment, support member pairs 103, 104 and 106,108 may be compressed for insertion into a catheter lumen by a device that increases the distance between apex 193 and apex 195. Such a device could be a tool with spreading jaws, or a tapered member inserted between the apexes. The device could be left in engagement after insertion into the catheter, and then withdrawn to allow support member pairs 103-104 and 106-108 to move apart and engage their anchors into the wall of the air passageway.

For removal, a retractor device is deployed from a catheter lumen to engage apex 193 and 195, and restrain intra-bronchial device 190. The retractor device may be any device that fits into the space defined by apexes 193 and 195 when the intra-bronchial device 190 is in its fully deployed configuration. The retractor device is used to increase the distance between apexes 193 and 195 until anchors 113, 114, 116, and 118, and anchor ends 123, 124, 126, and 128 are released from the air passageway wall. This collapses the anchors into to the first configuration for removal. Intra-bronchial device 190 is then further collapsed, and drawn into the catheter by pulling on the retractor device. This additionally collapses support structure 101 and obstructing member 110 into the first position so that they may be fully drawn into the catheter. Once drawn into the catheter, intra-bronchial device 190 may be removed from the air passageway and the patient.

FIG. 18 is a perspective view illustrating an alternative embodiment of a removable intra-bronchial device 200 with both distal and proximal anchors carried on corresponding peripheral portions of central support structure 109 in accord with the present invention. FIG. 19 is a side view of the device 200 of FIG. 18. Intra-bronchial device 200 is generally similar in construction, placement, and operation to intra-bronchial device 150 of FIGS. 9-11. Intra-bronchial device 200 is removed in the manner described in conjunction with FIG. 7. Intra-bronchial device 200 differs from intra-bronchial device 150 in that the central support structure 109 carries distal anchors in addition to the proximal anchors of device 150. Intra-bronchial device 200 includes distal anchors 212, 213, 214, 216, and 218; anchor ends 222, 223, 224, 226, and 228; and stops 252, 253, 254, 256, and 258. Intra-bronchial device 200 also include two more proximal anchors than device 150, which are proximal anchors 113 and 118; anchor ends 123 and 128, and stops 153 and 158.

The central support structure 109 of support structure 101 extends both distally and proximally of obstructing member 110, and carries both the proximal anchors 112, 113, 114, 116, and 118 and distal anchors 212, 213, 214, 216, and 218. The support structure 101 also includes support members 102, 103, 104, 106, and 108. Because of the perspective of FIGS. 18 and 19, several of the anchor members and several of the support members are not visible. Intra-bronchial device 200 is expected to provide additional anchoring force compared to the other embodiments disclosed herein.

Although the present invention has been described in considerable detail with reference to certain preferred embodiments, other embodiments are possible. Therefore, the spirit or scope of the appended claims should not be limited to the description of the embodiments contained herein. It is intended that the invention resides in the claims hereinafter appended.

What is claimed is:

1. An intra-bronchial device for placement in an air passageway of a lung, the device comprising:
    a generally umbrella-shaped obstructing member configured when deployed to substantially seal and preclude air from being inhaled into an air passageway while allowing fluid to flow past and around the obstructing member in an expiratory direction through the air passageway;
    a first anchor positioned distally of the mid-point of the obstructing member and terminating at a plurality of first anchor tips;
    a second anchor positioned proximally of the mid-point of the obstructing member and terminating at a plurality of second anchor tips; and
    a support structure having a distal end and a proximal end, the support structure positioned between the first anchor and the second anchor, wherein at least one of the first anchor tips is positioned distally to the distal end of the support structure;
    wherein the first and the second anchors are configured to prevent substantial migration of the device within the air passageway when the anchors are deployed, and are releasable to permit removal of the device from said passageway.

2. The intra-bronchial device of claim 1, wherein the support structure is attached to the obstructing member, the first and second anchors attached to the support structure.

3. The intra-bronchial device of claim 2, wherein at least a portion of the support structure is configured to be collapsed.

4. The intra-bronchial device of claim 1, wherein the first anchor is configured to pierce a surface of a wall of the air passageway.

5. The intra-bronchial device of claim 1, wherein the second anchor is configured to pierce a surface of a wall of the air passageway.

6. The intra-bronchial device of claim 1, wherein at least one of the first and second anchors includes a stop configured to limit the penetration of the anchor into a wall of the air passageway.

7. The intra-bronchial device of claim 1, wherein one of the first and the second anchors is configured to move from a first position to a second position to engage the air passageway.

8. The intra-bronchial device of claim 1, wherein at least one of the first and second anchors is configured to move from a first position to a second position to engage the air passageway, and to move from the second position to the first position to disengage the air passageway.

9. The intra-bronchial device of claim 1, wherein the obstructing member and at least one of the first and second anchors are configured to be deployed simultaneously.

10. The intra-bronchial device of claim 1, wherein the anchors include a resilient material for imparting a securing force to the air passageway to deform the air passageway.

11. The intra-bronchial device of claim 1, wherein the obstructing member comprises a flexible membrane.

12. The intra-bronchial device of claim 1, wherein at least one of the first and second anchors has an anchoring end configured to engage a wall of the air passageway.

13. The intra-bronchial device of claim 1, wherein the obstructing member allows air and mucus to travel past the obstructing member.

14. The intra-bronchial device of claim 1, wherein the obstructing member biases between a collapsed position and an expanded position.

15. The intra-brochial device of claim 1, wherein the obstructing member is generally parabolic.

16. The intra-bronchial device of claim 1, wherein a proximal portion of the obstructing member has a substantially cylindrical outer surface such that a substantial portion of the outer surface forms a contact zone with an interior surface of the air passageway of the lung when the device is placed in the air passageway.

17. The intra-bronchial device of claim 16, wherein the proximal portion defines an opening of the obstruction member.

18. The intra-bronchial device of claim 16, wherein a distal portion of the obstructing member tapers gradually inward.

19. The intra-bronchial device of claim 1, wherein the first anchor and second anchor each comprises at least three outwardly extending anchoring members.

20. The intra-bronchial device of claim 1, wherein the support structure comprises hypodermic needle tubing.

21. The intra-bronchial device of claim 1, wherein the support structure comprises a first peripheral portion and a second peripheral portion with at least a portion of the obstructing member positioned therebetween, the first anchor carried on the first peripheral portion and the second anchor carried on the second peripheral portion of the support structure.

22. The intra-bronchial device of claim 21, wherein the support structure comprises a plurality of elongate support members and a central support member, the plurality of elongate support members extend radially from the central support member, the central support member defines the first and second peripheral portions.

23. An intra-bronchial device comprising:
an obstructing member comprising a flexible solid membrane supported by a support frame, the flexible membrane being generally umbrella-shaped and configured to be implanted in an air passageway to substantially prevent air from flowing in a first direction past the obstructing member while substantially allowing fluid to flow around and past the obstructing member in an opposite direction;
a first anchor connected distal to one end of the obstructing member and extending in a first direction relative to the flexible membrane, the first anchor terminating at a plurality of first anchor tips;
a second anchor connected proximal to the other end of the obstructing member and extending in a second direction relative to the flexible membrane, which second direction is generally opposite to the first direction, and the second anchor terminating at a plurality of second anchor tips; and
a support structure having a distal end and a proximal end, the support structure positioned between the first anchor and the second anchor, wherein at least one of the first anchor tips is positioned distally to the distal end of the support structure;
wherein the first and second anchors are configured to substantially anchor the device within the air passageway when the anchors are deployed.

24. The intra-bronchial device of claim 23, wherein the support structure extends axially from the obstructing member, and at least one of the first anchor and the second anchor comprises a plurality of elongated members each extending radially from the support structure.

25. The intra-bronchial device of claim 23, wherein the support structure comprises an elongated body between the proximal end and the distal end of the support structure, the obstructing member carried by the elongated body, the first anchor attached to the distal end of the support structure, and the second anchor attached to the proximal end of the support structure.

26. The intra-bronchial device of claim 23, wherein the obstructing member is configured to be moved radially between an unexpanded position and an expanded position while the first and second anchors prevent substantial migration of the device in the air passageway.

27. The intra-bronchial device of claim 23, wherein the intra-bronchial device is configured for deployment through a minimally invasive access delivery device when the obstructing member and anchors are in a collapsed position.

28. The intra-bronchial device of claim 23, wherein the obstructing member is positioned between the first anchor and the second anchor.

29. The intra-bronchial device of claim 23, wherein a proximal portion of the obstructing member has a substantially cylindrical outer surface such that a substantial portion of the outer surface forms a contact zone with an interior surface of the air passageway of the lung when the device is placed in the air passageway.

30. An intra-bronchial device for placement in an air passageway of a lung, the device comprising:
a generally umbrella-shaped obstructing member configured to substantially seal and prevent air from being inhaled into an air passageway while allowing fluid to substantially flow around and past the obstructing member in the opposite direction through the air passageway;
a first set of anchors connected to the obstructing member and terminating at a plurality of first anchor tips;
a second set of anchors connected to the obstructing member and terminating at a plurality of second anchor tips, the first set of anchors spaced distally from the second set of anchors; and
a support structure having a distal end and a proximal end, the support structure positioned between the first set of anchors and the second set of anchors, wherein at least one of the first anchor tips is positioned distally to the distal end of the support structure.

31. The intra-bronchial device of claim 30, wherein the obstructing member is positioned in a space defined between the first set of anchors and the second set of anchors.

32. The intra-bronchial device of claim 30, wherein the support structure comprises a first portion and a second portion, at least a portion of the obstructing member being positioned between the first and the second portions of the support structure, and the first set of anchors being carried on the first portion of the support structure and the second set of anchors carried on the second portion of the support structure.

33. An intra-bronchial device for placement in an air passageway of a lung, the device comprising:
an obstructing member configured when deployed to substantially seal against a wall of the air passageway and preclude fluid flow in at least one direction past the obstructing member, the obstructing member being generally umbrella-shaped;
a first anchor positioned at one end of the obstructing member and terminating at a plurality of first anchor tips;
a second anchor positioned at the other end of the obstructing member and terminating at a plurality of second anchor tips; and
a support structure having a distal end and a proximal end, the support structure positioned between the first anchor and the second anchor, wherein at least one of the first anchor tips is positioned distally to the distal end of the support structure;
wherein the first and the second anchors are configured to prevent substantial migration of the device within the air passageway when the anchors are deployed and are releasable to permit removal of the device from said passageway.

34. An intra-bronchial device for placement in an air passageway of a lung, the device comprising:

a generally umbrella-shaped obstructing member configured when deployed to substantially seal and preclude air from being inhaled into an air passageway while allowing fluid to flow around the obstructing member in an expiratory direction through the air passageway;

at least one anchor positioned distally of the mid-point of the obstructing member, the at least one anchor adapted to extend laterally outward beyond the obstructing member and adapted to form a substantially perpendicular angle with an axial center of a central support structure in connection with the obstructing member;

the at least one anchor configured to prevent substantial migration of the device within the air passageway when the at least one anchor is deployed; and the at least one anchor releasable to permit removal of the device from said air passageway.

35. The intra-bronchial device of claim 34, wherein the at least one anchor further comprises at least a first and a second inflection points configured to reduce strain.

* * * * *

UNITED STATES PATENT AND TRADEMARK OFFICE
CERTIFICATE OF CORRECTION

PATENT NO. : 7,875,048 B2
APPLICATION NO. : 10/933778
DATED : January 25, 2011
INVENTOR(S) : David H. Dillard et al.

Page 1 of 1

It is certified that error appears in the above-identified patent and that said Letters Patent is hereby corrected as shown below:

Title Page, Item (56) Other Pubs.
In column 2 (page 4, Other Publications) at line 13, Change "Intertracheal" to --Intratracheal--.

Title Page, Item (56) Other Pubs.
In column 2 (page 4, Other Publications) at line 22, Change "Cyanocrylate" to --Cyanoacrylate--.

Title Page, Item (56) Other Pubs.
In column 2 (page 4, Other Publications) at line 37, Change "Instiute," to --Institute,--.

In column 14 at line 57, In Claim 15, change "intra-brochial" to --intra-bronchial--.

Signed and Sealed this
Sixteenth Day of August, 2011

David J. Kappos
*Director of the United States Patent and Trademark Office*